United States Patent
Kem et al.

(10) Patent No.: US 9,440,948 B2
(45) Date of Patent: Sep. 13, 2016

(54) NICOTINE COMPOUNDS AND ANALOGS THEREOF, SYNTHETIC METHODS OF MAKING COMPOUNDS, AND METHODS OF USE

(75) Inventors: William Reade Kem, Gainesville, FL (US); Ferenc Soti, Gainesville, FL (US); Anne Rouchaud, Brussels (BE); Hong Xing, Gainesville, FL (US); Jon Lindstrom, Radnor, PA (US); Kristin Marie Andrud, Lakewood, CO (US)

(73) Assignees: UNIVERSITY OF FLORIDA RESEARCH FOUNDATION, INC., Gainesville, FL (US); THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 44 days.

(21) Appl. No.: 13/819,067

(22) PCT Filed: Sep. 2, 2011

(86) PCT No.: PCT/US2011/050362
§ 371 (c)(1),
(2), (4) Date: Mar. 4, 2013

(87) PCT Pub. No.: WO2012/031220
PCT Pub. Date: Mar. 8, 2012

(65) Prior Publication Data
US 2013/0157995 A1 Jun. 20, 2013

Related U.S. Application Data

(60) Provisional application No. 61/379,962, filed on Sep. 3, 2010.

(51) Int. Cl.
*A61K 31/465* (2006.01)
*C07D 401/04* (2006.01)
*C07D 401/12* (2006.01)

(52) U.S. Cl.
CPC ........... *C07D 401/04* (2013.01); *C07D 401/12* (2013.01)

(58) Field of Classification Search
CPC .......................... A61K 31/465; C07D 401/04
USPC ........................................ 514/343; 546/279.4
See application file for complete search history.

(56) References Cited

U.S. PATENT DOCUMENTS 4,163,855 A  8/1979 Secor et al.
5,498,793 A  3/1996 Mantegazza et al.
(Continued)

FOREIGN PATENT DOCUMENTS

WO  2005023942  3/2005
WO  2005077897  8/2005
(Continued)

OTHER PUBLICATIONS

International Search Report and Written Opinion dated Apr. 16, 2012.
(Continued)

*Primary Examiner* — Brenda Coleman
(74) *Attorney, Agent, or Firm* — Thomas | Horstemeyer, LLP

(57) ABSTRACT

Embodiments of the present disclosure provide for compounds such as those shown in FIG. 1.1 (compounds A, B, C, and D), 2'substituted nicotine compounds, azetidine compounds, ether linked nicotine compounds (FIG. 1.2, compounds E, F, G, and H), methods of synthesis of the compounds, methods of treatment of a condition using compounds A, B, C, D, 2'substituted nicotine compounds, azetidine compounds, or ether linked nicotine compounds, methods of selectively stimulating alpha7 nAChR and/or alpha4beta2 receptors, and the like.

FIG. 1.1

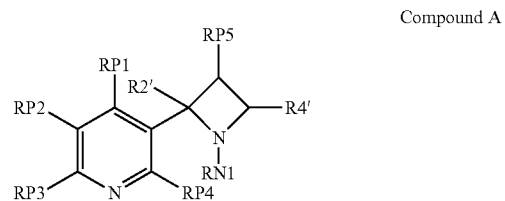

Compound A

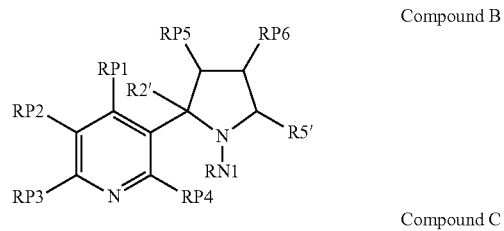

Compound B

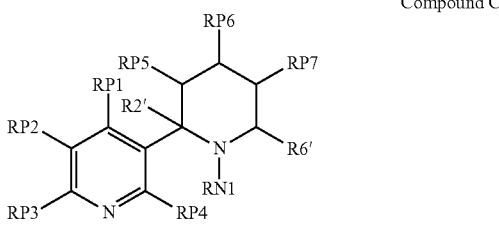

Compound C

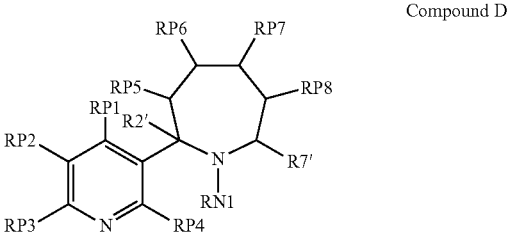

Compound D

10 Claims, 19 Drawing Sheets

(56) References Cited

U.S. PATENT DOCUMENTS

| | | |
|---|---|---|
| 5,516,782 A | 5/1996 | Becker et al. |
| 5,516,785 A | 5/1996 | Zoltewicz et al. |
| 5,594,011 A | 1/1997 | McDonald et al. |
| 5,602,257 A | 2/1997 | Zoltewicz et al. |
| 5,629,325 A | 5/1997 | Lin et al. |
| 5,741,802 A | 4/1998 | Kem et al. |
| 5,840,906 A | 11/1998 | Zoltewicz et al. |
| 5,914,328 A | 6/1999 | Lin et al. |
| 5,948,793 A | 9/1999 | Abreo et al. |
| 5,977,144 A | 11/1999 | Meyer et al. |
| 6,437,138 B1 | 8/2002 | Lin et al. |
| 6,630,491 B1 | 10/2003 | Zoltewicz et al. |
| 8,445,478 B2 | 5/2013 | Sabuco |
| 2009/0297443 A1 | 12/2009 | Mukherjee et al. |
| 2013/0045963 A1 | 2/2013 | Rodgers et al. |
| 2013/0137697 A1 | 5/2013 | Papke et al. |

FOREIGN PATENT DOCUMENTS

| | | |
|---|---|---|
| WO | 2007062193 | 5/2007 |
| WO | 2007143823 | 12/2007 |
| WO | 2011022467 | 2/2011 |
| WO | 2012054721 | 4/2012 |

OTHER PUBLICATIONS

European Search Report; European Patent Office, 80298 Munich, Germany; Feb. 6, 2014; 4 pages.

David X. Wang, et al.; Structure-Activity Relationships for Nicotine Analogs Comparing Competition for [3H] Nicotine Binding and Psychotropic Potency; 1998 Wiley-Liss, Inc.; Department of Pharmacology and Physiology, University of Tochester Medical Center, Rochester, New York.

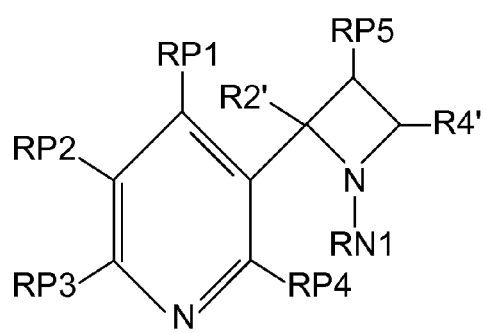
Compound A
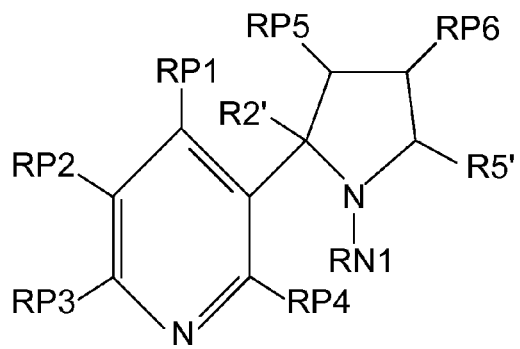
Compound B
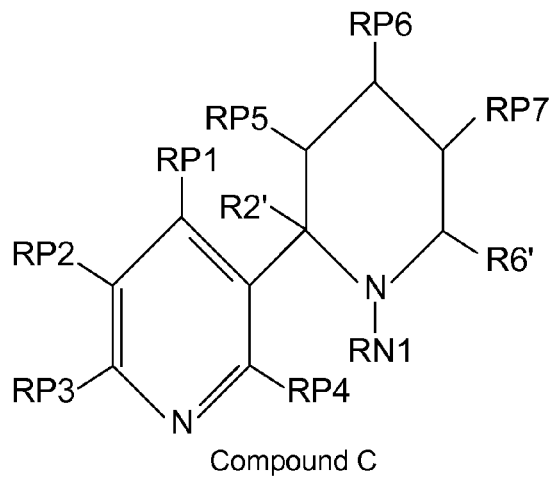
Compound C
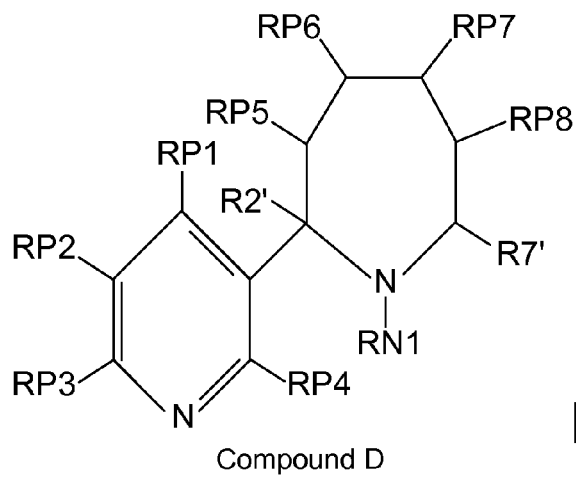
Compound D
FIG. 1.1

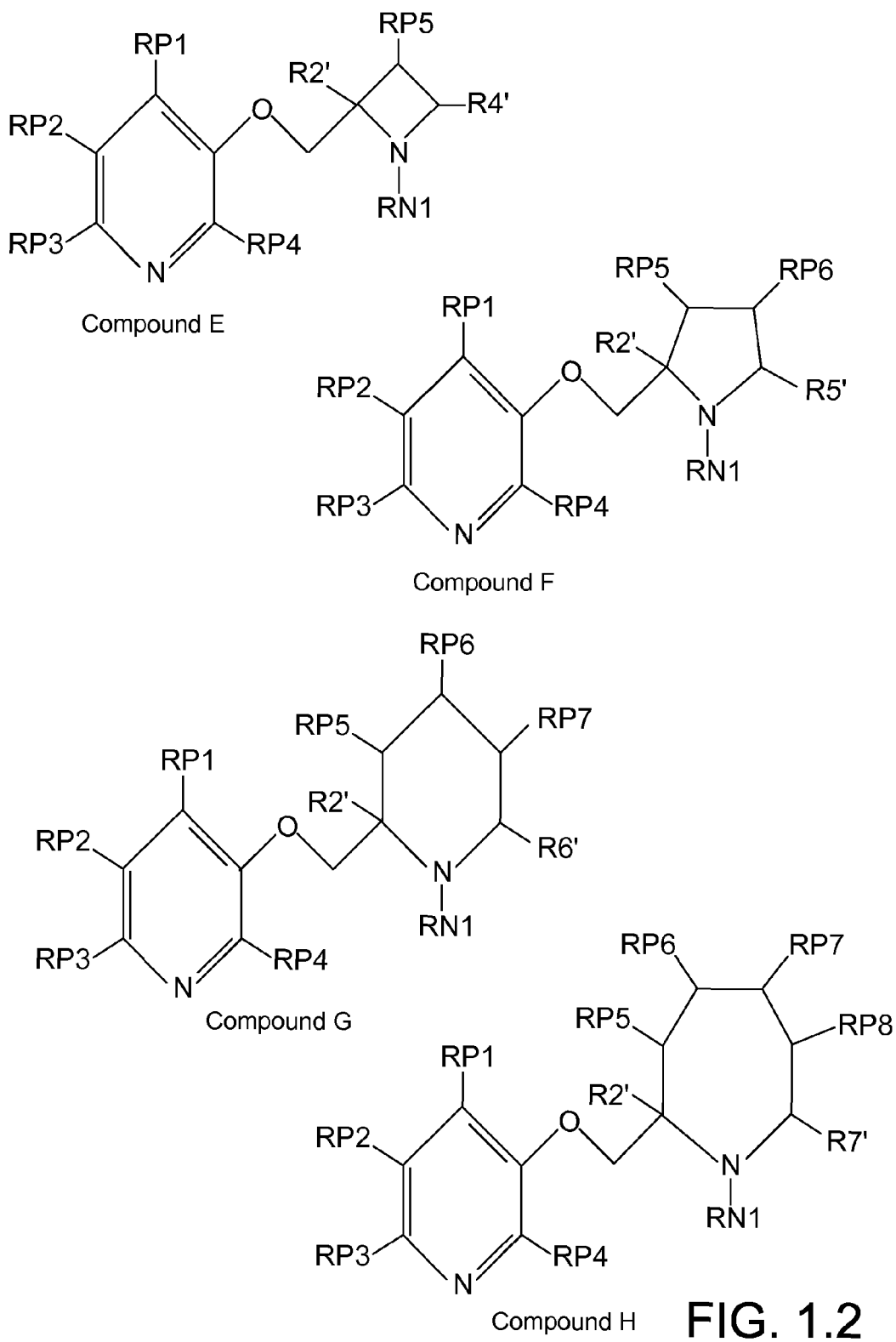
FIG. 1.2

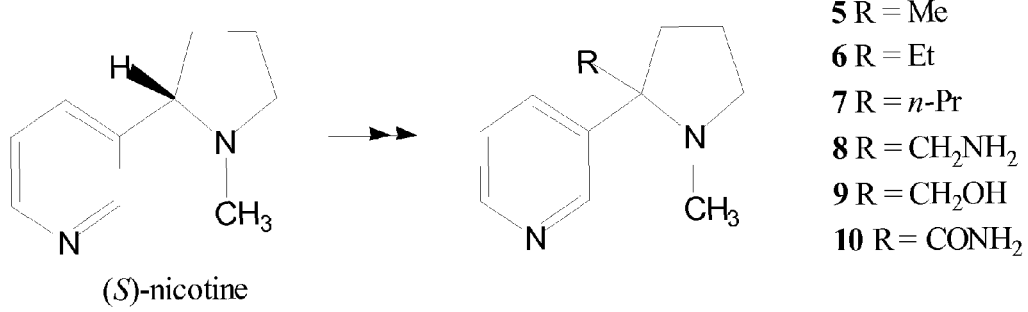
FIG. 2.1

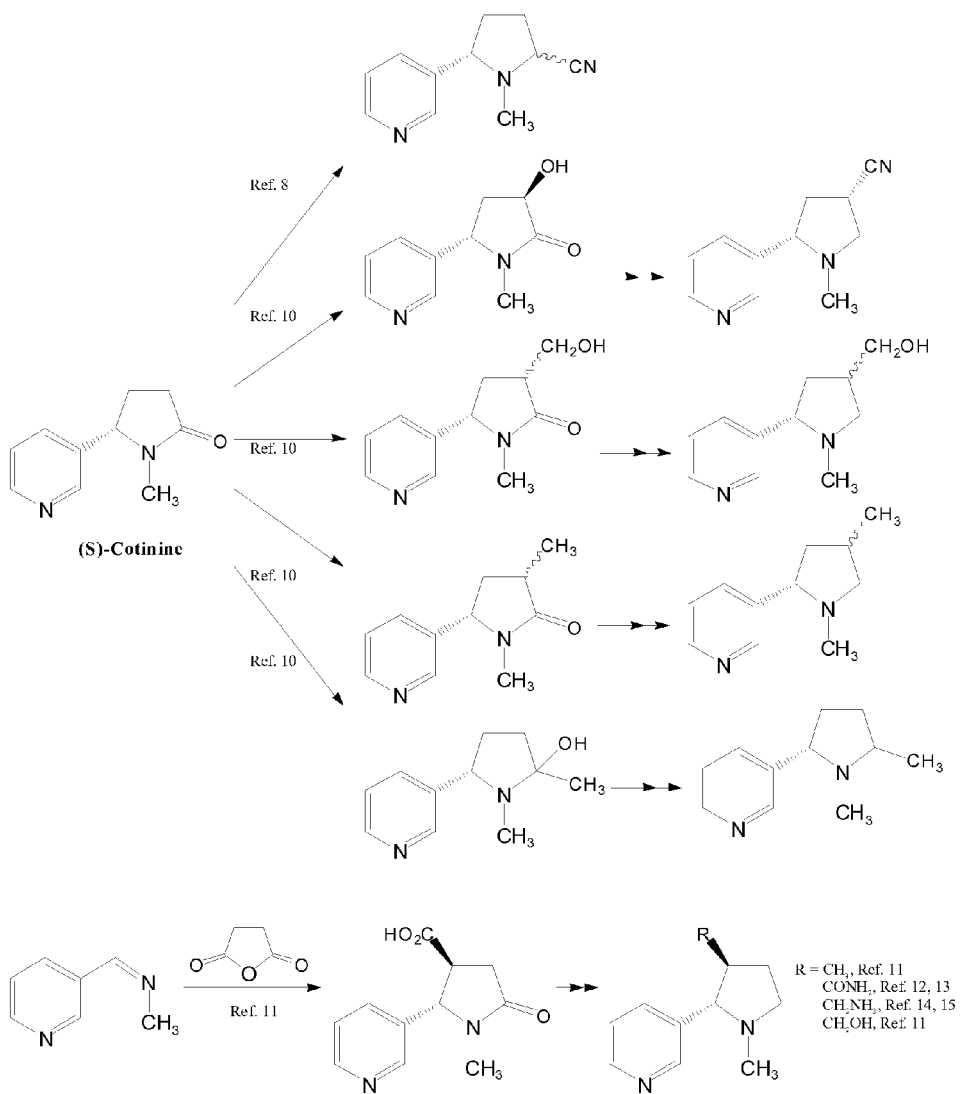
FIG. 2.2
Scheme 1

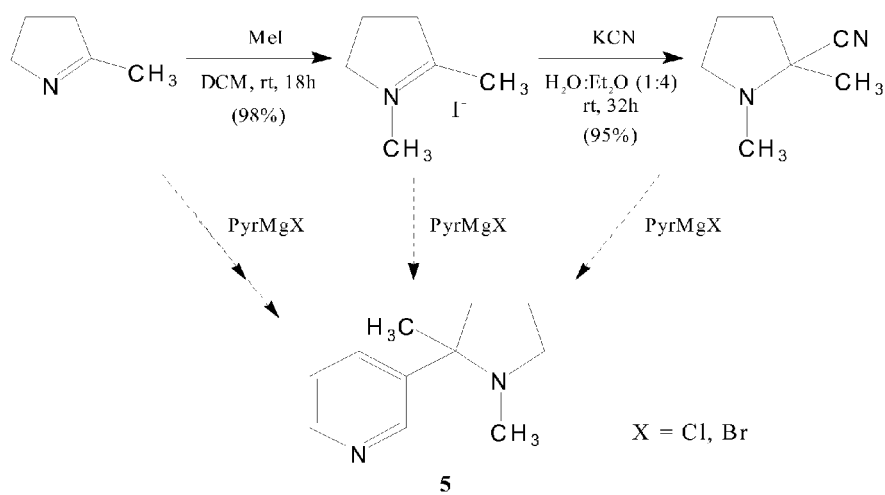
FIG. 2.3
Scheme 2
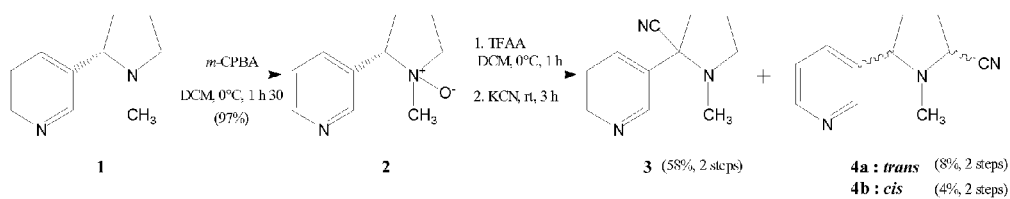
FIG. 2.4
Scheme 3

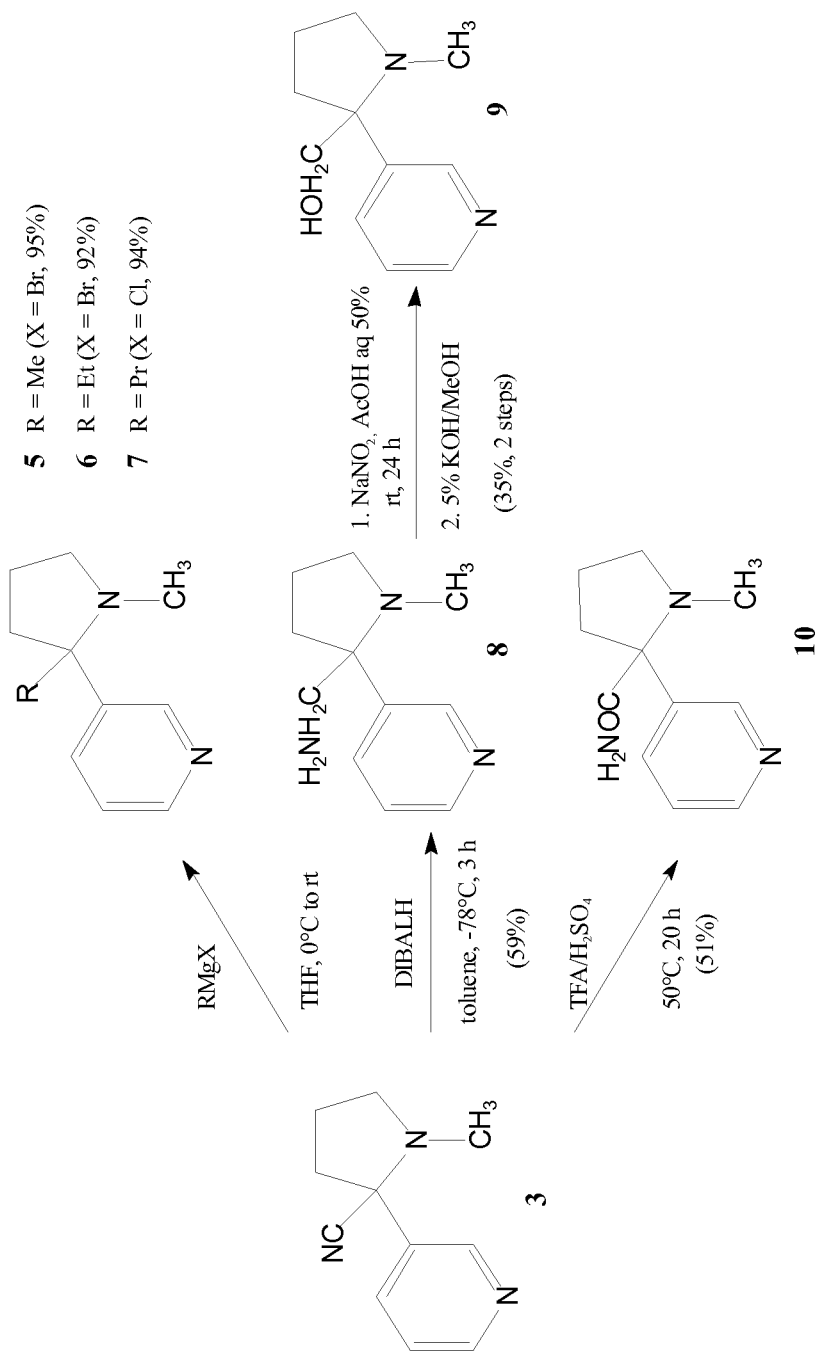
FIG. 2.5
Scheme 4

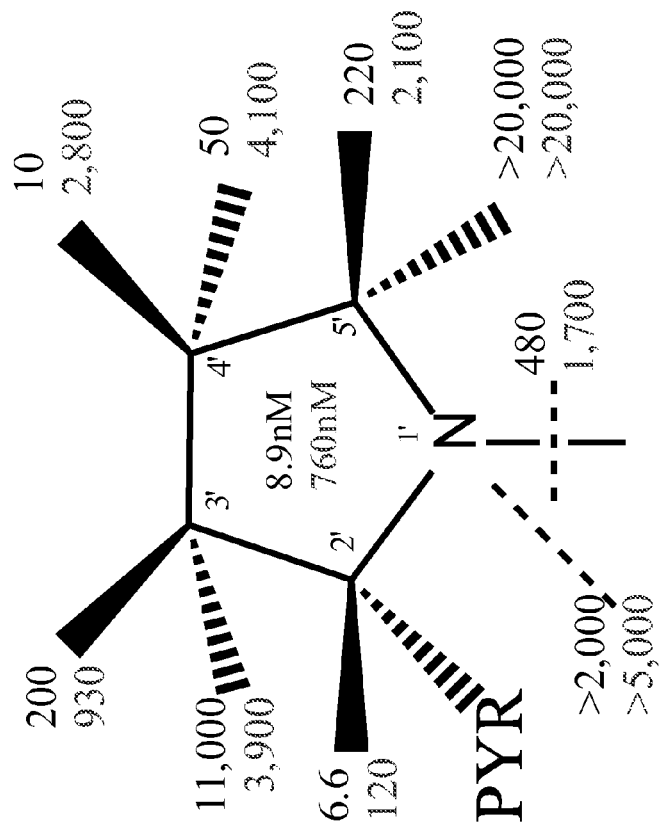
FIG. 2.6
Ki s for binding to rat alpha4beta2 (TOP) and alpha7 (Bottom) nAChRs determined with radiolabeled cytisine and alpha-bungarotoxin, respectively (The numbers for (S)-nicotine are shown within the ring).

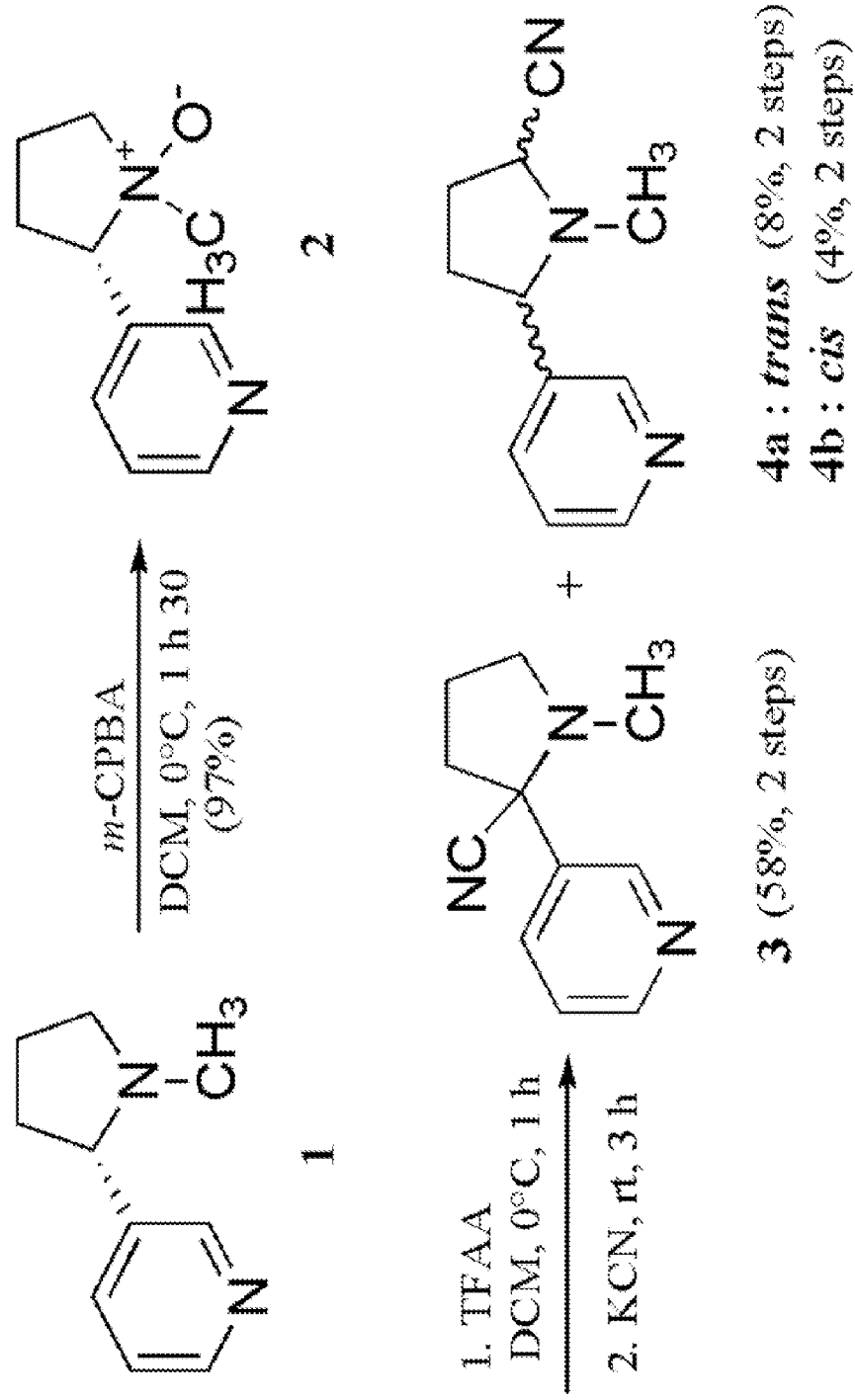
FIG. 2.7

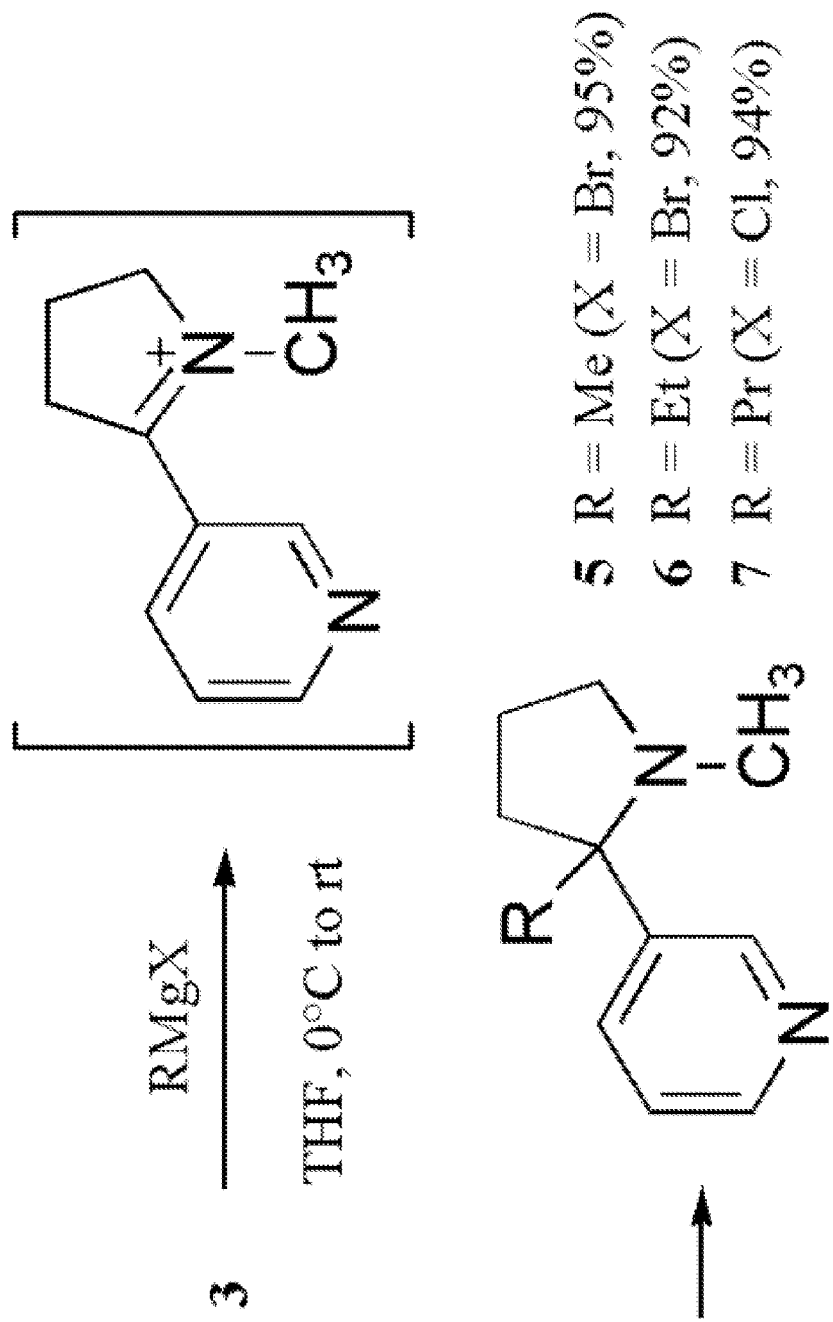
FIG. 2.8

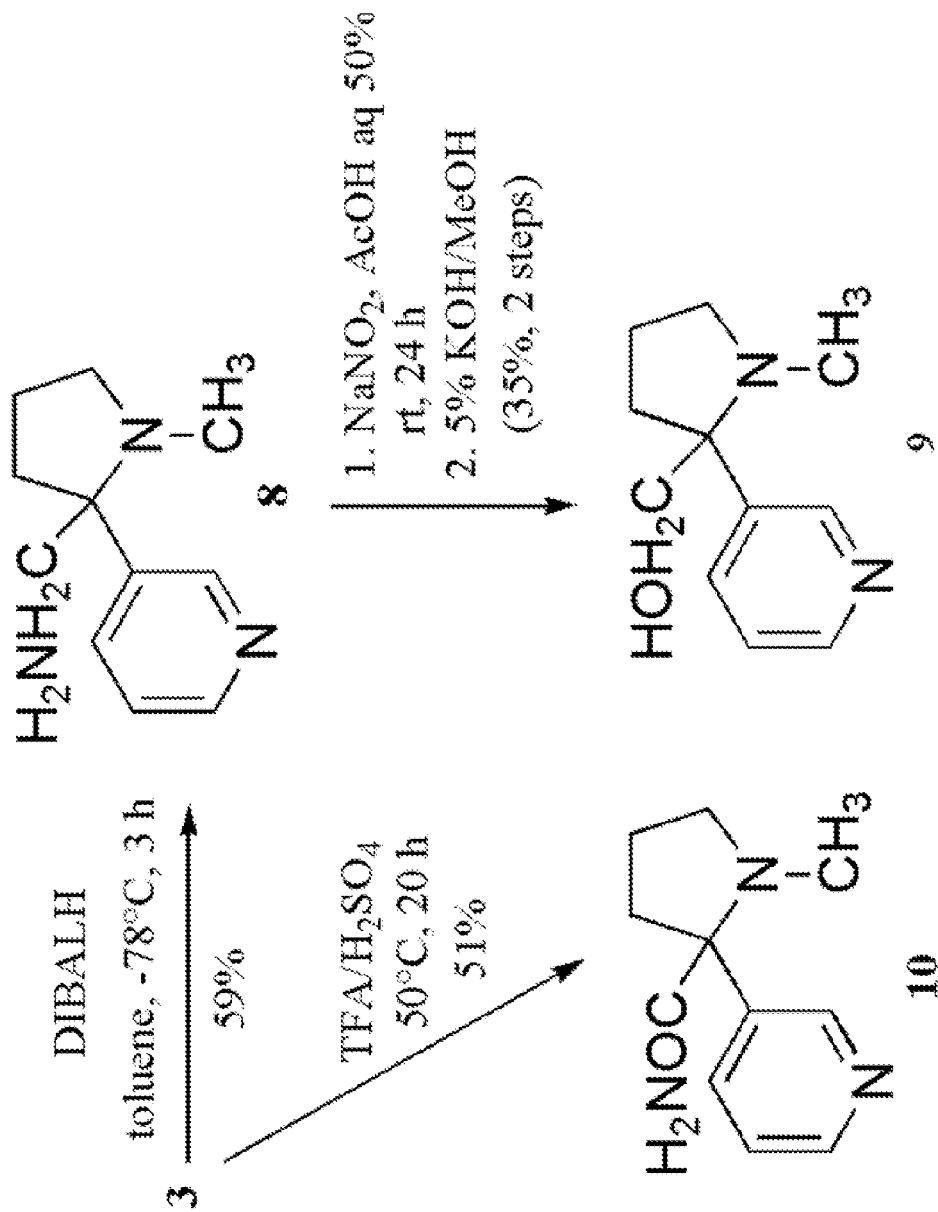
FIG. 2.9

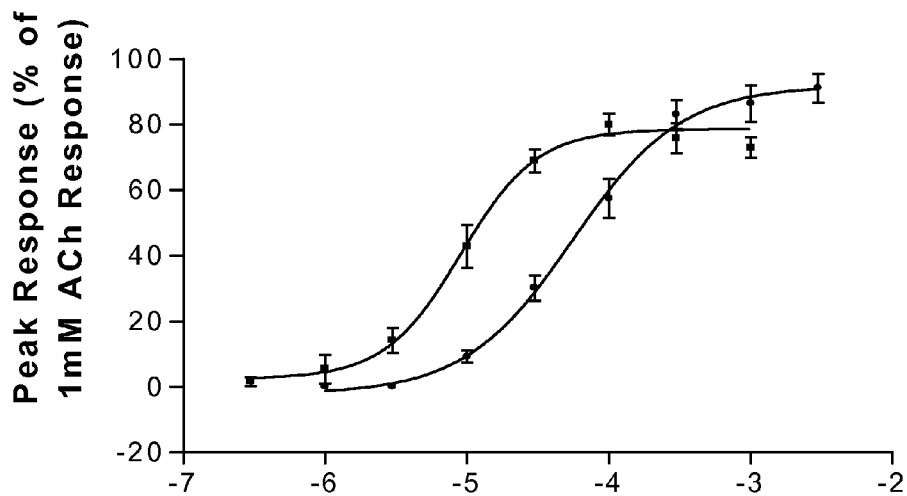
FIG. 2.10
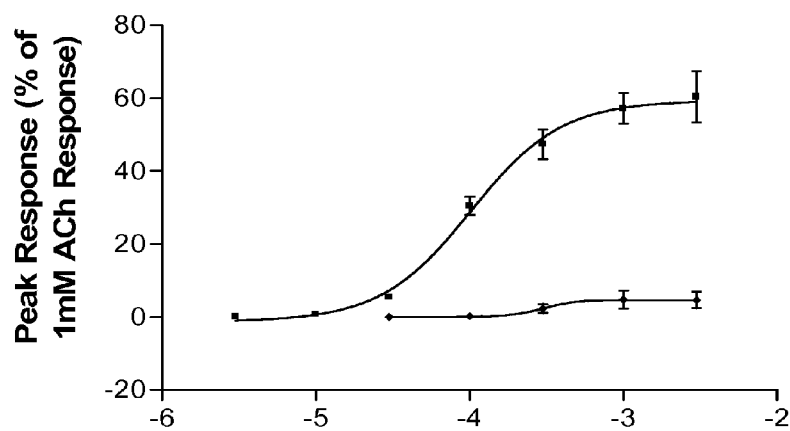
FIG. 2.11

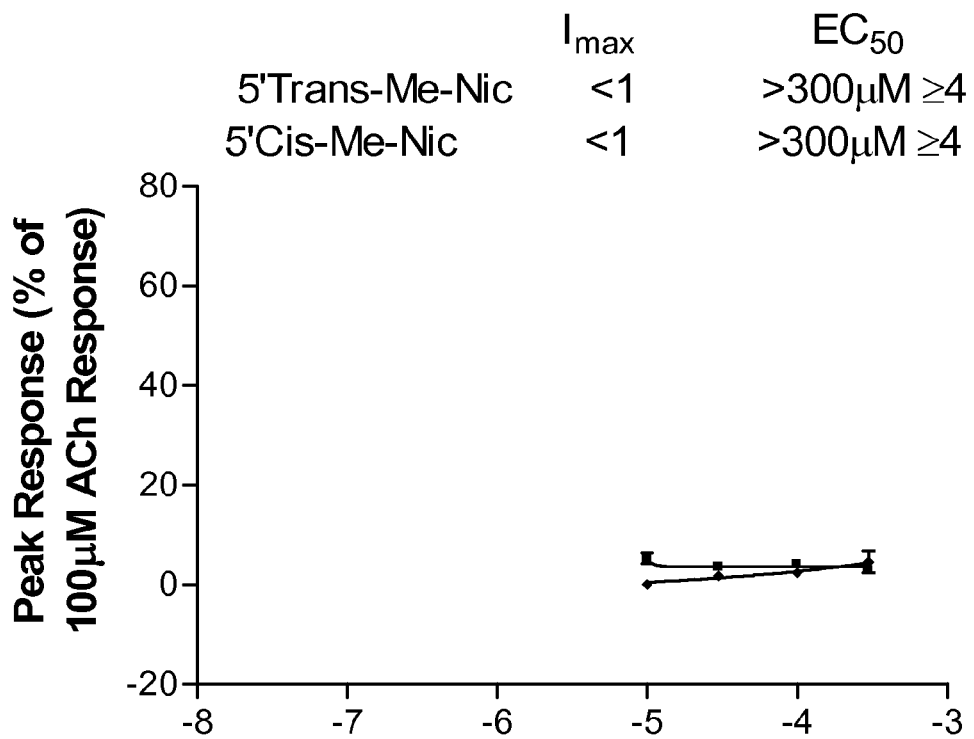
FIG. 2.12
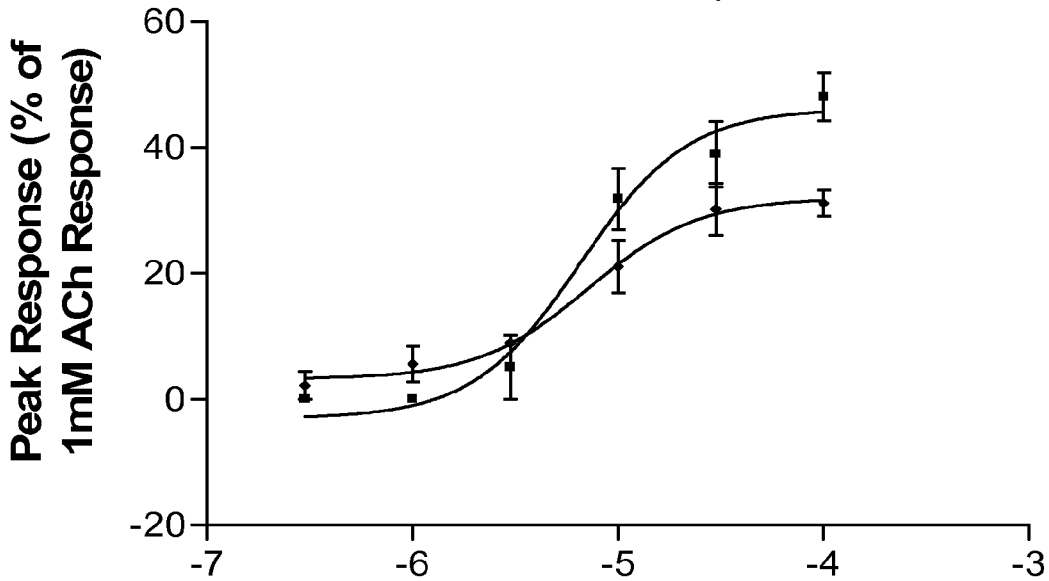
FIG. 2.13

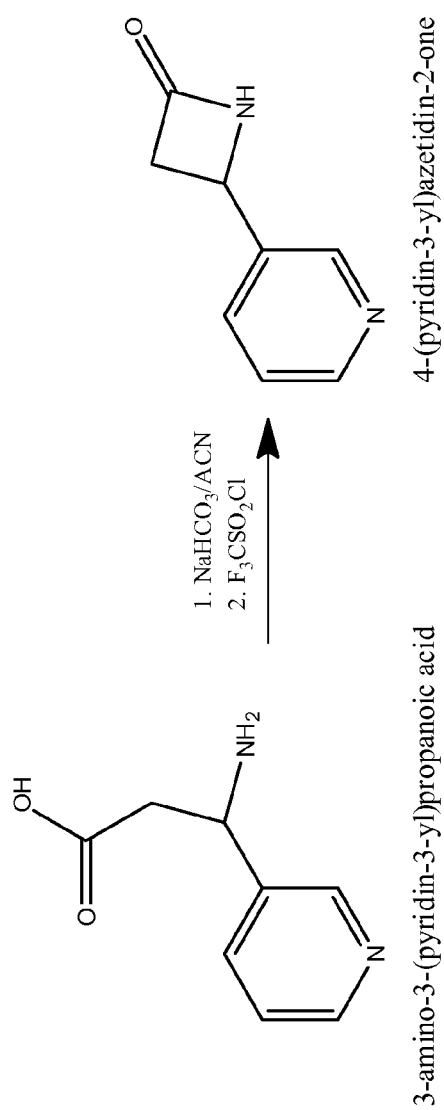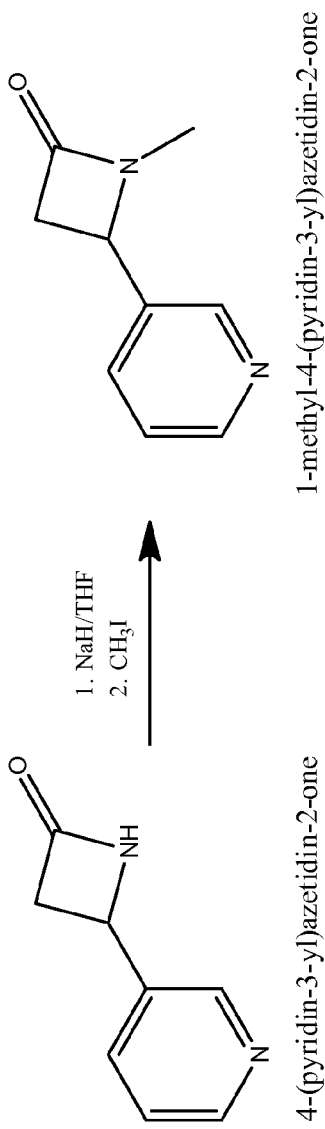
FIG. 3.1
FIG. 3.2

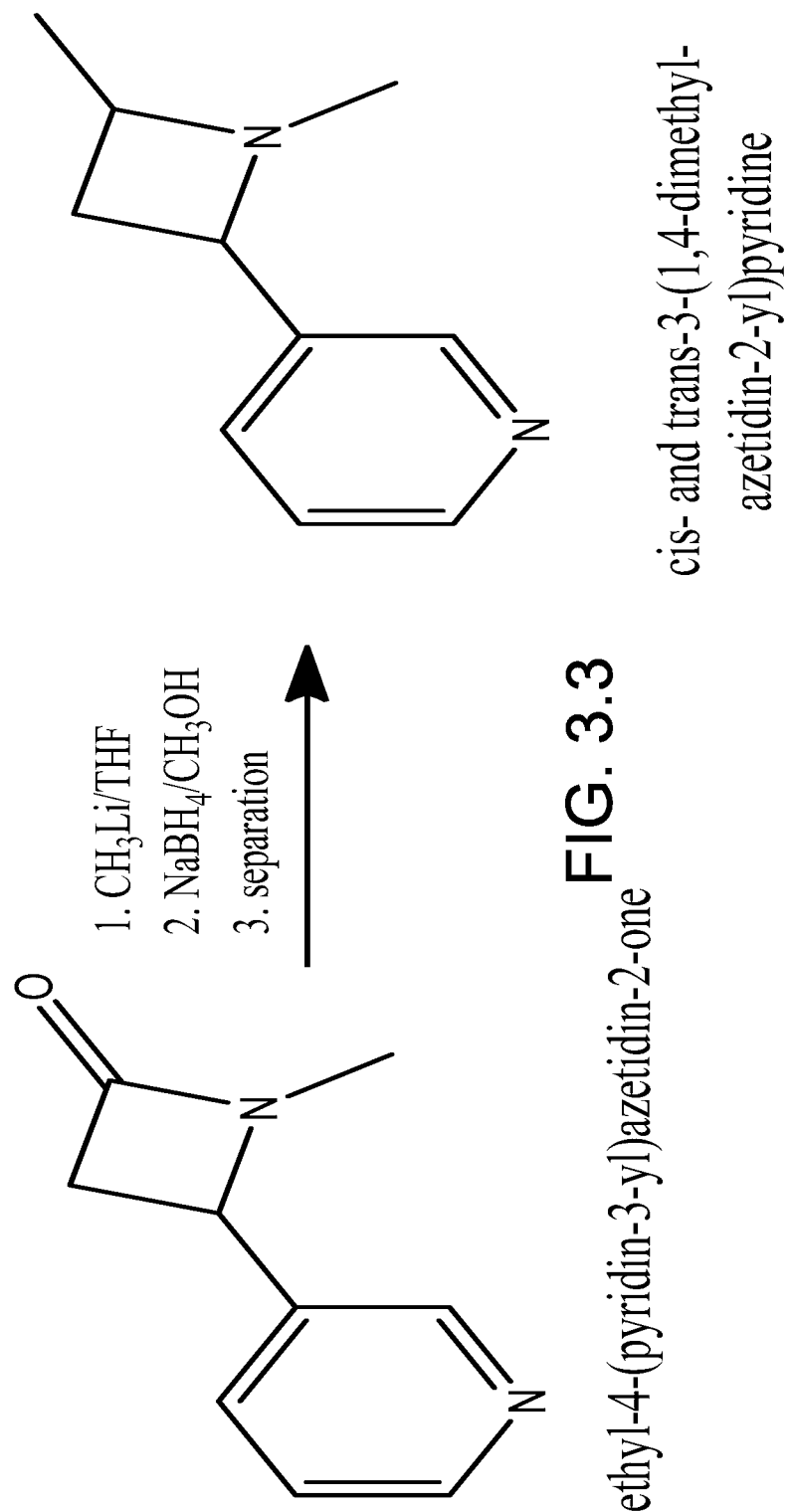
FIG. 3.3

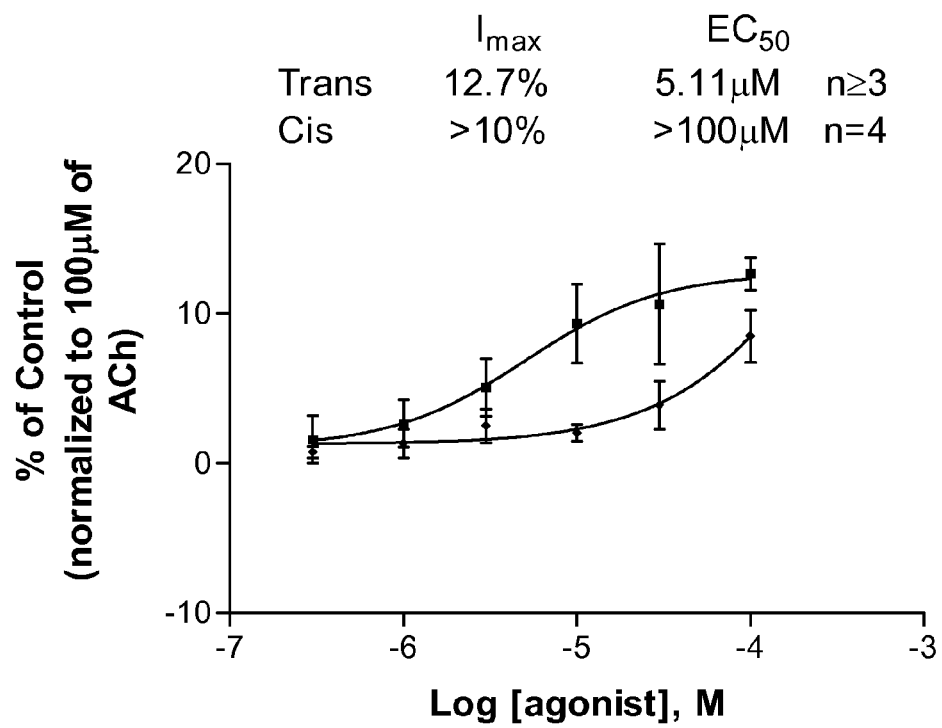
FIG. 3.4
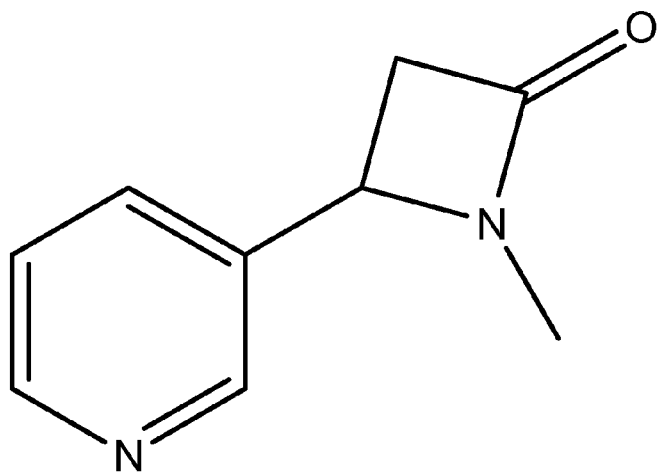
1-methyl-4-(pyridin-3-yl)azetidin-2-one
FIG. 3.5

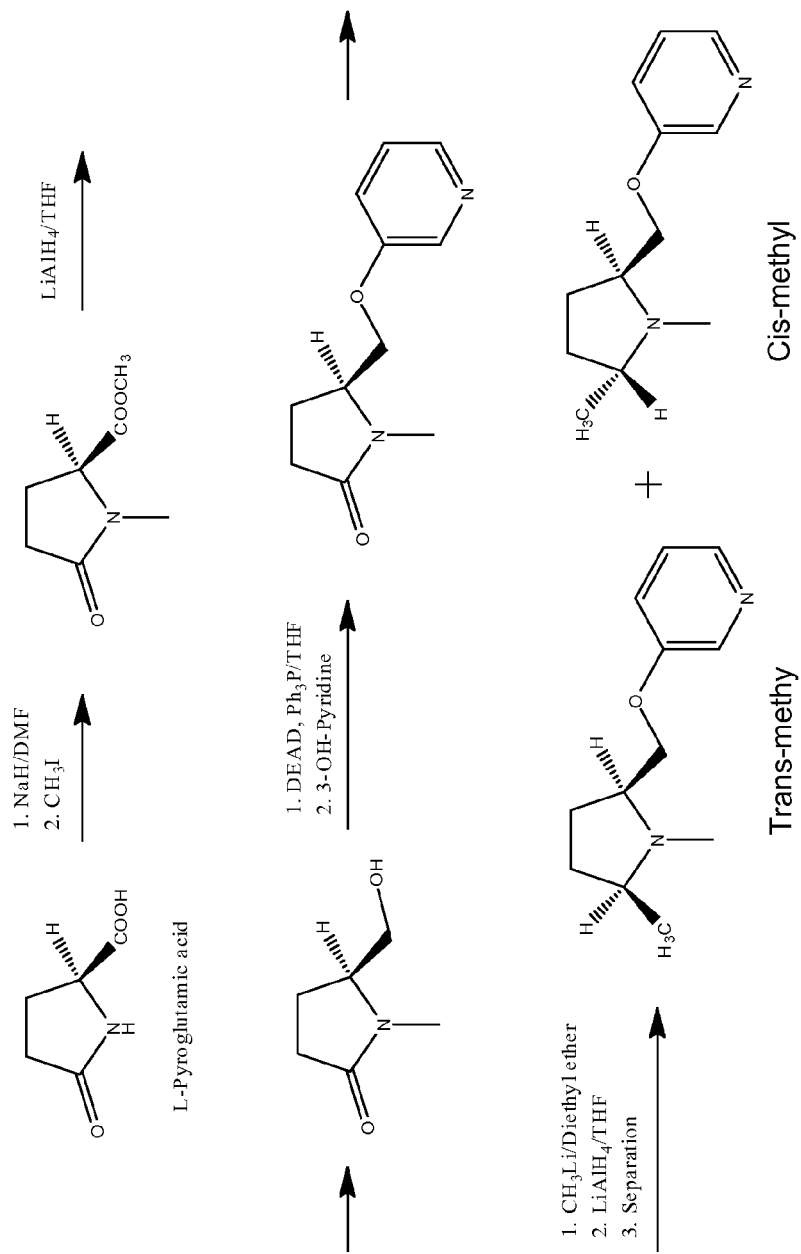
FIG. 4.1

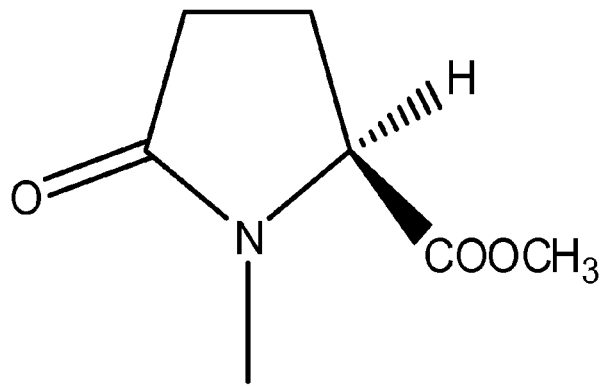
(S)-methyl 1-methyl-5-oxopyrrolidine-2-carboxylate
FIG. 4.2
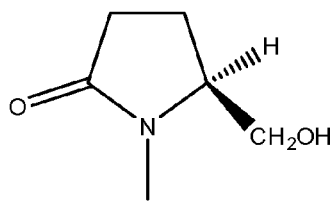
FIG. 4.3
(S)-5-(hydroxymethyl)-1-methylpyrrolidin-2-one
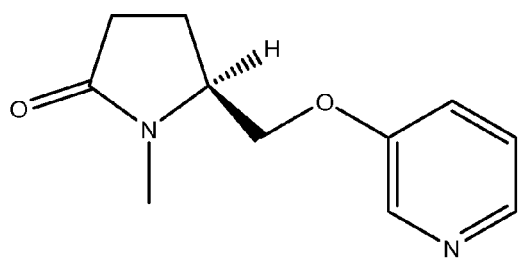
FIG. 4.4
(S)-1-methyl-5-((pyridin-3-yloxy)methyl)pyrrolidin-2-one

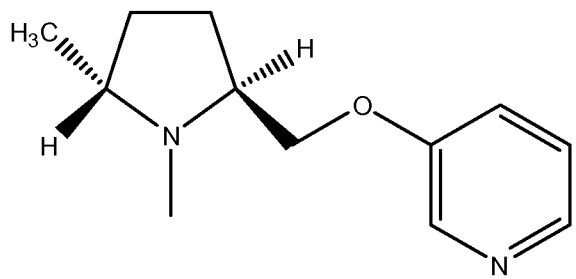
3-(((2S,5R)-1,5-dimethylpyrrolidin-2-yl)methoxy)pyridine
FIG. 4.5
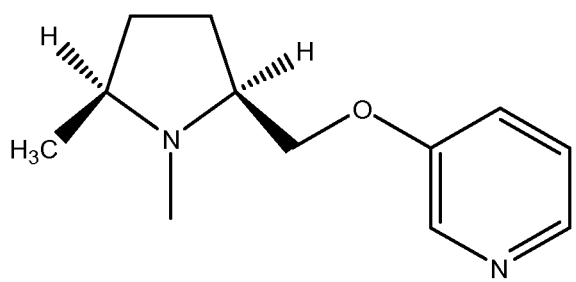
3-(((2S,5S)-1,5-dimethylpyrrolidin-2-yl)methoxy)pyridine
FIG. 4.6

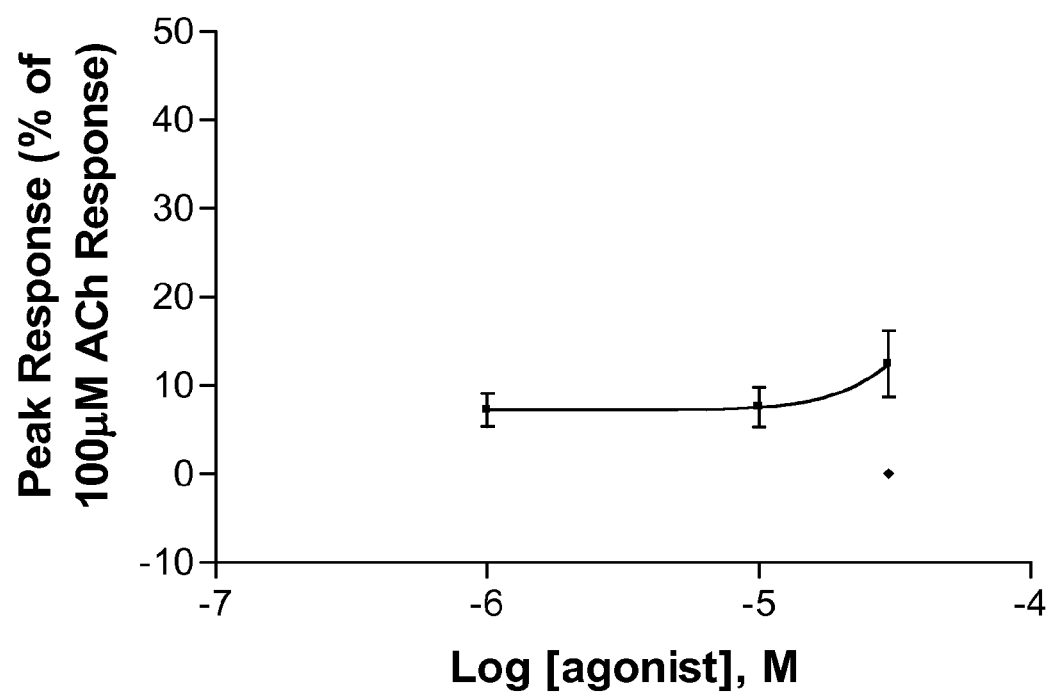
FIG. 4.7

NICOTINE COMPOUNDS AND ANALOGS THEREOF, SYNTHETIC METHODS OF MAKING COMPOUNDS, AND METHODS OF USE

CROSS-REFERENCE TO RELATED APPLICATION(S)

This application is the 35 U.S.C. §371 national stage of PCT application PCT/US2011/50362, filed Sep. 2, 2011 which claims priority to and the benefit of U.S. Provisional Application Ser. No. 61/379,962, filed Sep. 3, 2010, both of which are hereby incorporated by reference herein in their entirety.

STATEMENT OF GOVERNMENTAL SUPPORT

This invention was made with government support under grant number 5RO1MH61412, awarded by the National Institutes of Health (NIH) of the United States government. The government has certain rights in the invention. The research was also partly funded by Grant BM013 Florida Biomedical Program administered by the Florida Department of Health.

BACKGROUND

Deficits in brain nicotinic acetylcholine receptor (nAChR) expression have been reported in neurodegenerative and mental diseases. Therefore, nicotinic acetylcholine agonists are being developed to alleviate these deficits. Nicotine addiction is also being treated with nAChR agonists, including nicotine. While a variety of nicotine analogs have been synthesized and investigated using radioligand binding measurements (Wang et al., 1994; Lin et al., 1994; Lin et al., 1995; others), a comparative analysis of their functional effects (ability to activate) on alpha4beta2 and other brain nAChRs has not yet been made. Earlier studies reporting the consequence of structural modification of nicotine focused upon alpha4beta2 receptors, which display exceptionally high affinity for nicotine. While this receptor plays an important role in nicotine addiction and in cognition, another homomeric alpha7 receptor also contributes to cognitive function and also to inflammatory cell function. Nicotinic drug design for the alpha4beta2 receptors has utilized nicotine's two ring structure as a lead scaffold to synthesize new drug candidates. Since nicotine displays a relatively low affinity for alpha7 nAChRs, its structure has not been considered a promising scaffold for the design of new drugs that affect this receptor.

SUMMARY

Embodiments of the present disclosure provide for compounds such as those shown in FIG. 1.1 (compounds A, B, C, and D), 2'substituted nicotine compounds, azetidine compounds, ether linked nicotine compounds (FIG. 1.2, compounds E, F, G, and H), methods of synthesis of the compounds, methods of treatment of a condition using the compounds, 2'substituted nicotine compounds, azetidine compounds, or ether linked nicotine compounds, methods of selectively stimulating alpha7 nAChR and/or alpha4beta2 receptors, and the like.

An embodiment of the composition, among others, includes one or a combination of a compound selected from: compound A, compound B, compound C, compound D, compound E, compound F, compound G, and compound H.

An embodiment of the pharmaceutical composition, among others, includes one or a combination of a compound selected from: compound A, compound B, compound C, compound D, compound E, compound F, compound G, and compound H, wherein the compound is present in a therapeutically effective amount to treat a condition.

An embodiment of the method of selectively stimulating alpha7 nAChR, among others, includes using (e.g., administering) R4', R5', R6' or R7', trans substituted compounds A, B, C, and D and compound E, F, G, and H, respectively, wherein compound A, compound B, compound C, compound D, compound E, compound F, compound G, and compound H are described herein, wherein R4', R5', R6' or R7' are selected from a group selected from: an alkyl group having from 1 to 6 carbons, an alkyl amino group having from 1 to 6 carbons, an alkyl group having a hydroxylic group and having from 1 to 6 carbons, and a methoxy group.

An embodiment of the method of selectively stimulating alpha7 nAChR and alpha4beta2 receptors, among others, includes using (e.g., administering) R2' substituted compound A, compound B, compound C, and compound D, respectively, wherein compound A, compound B, compound C, and compound D, are described herein, wherein R2' is from a group selected from: an alkyl group having from 1 to 6 carbons, an alkyl amino group having from 1 to 6 carbons, an alkyl group having a hydroxylic group and having from 1 to 6 carbons, and a methoxy group.

An embodiment of treating a condition, among others, includes administering an effective dose of one or more compounds selected from compound A, compound B, compound C, compound D, compound E, compound F, compound G, and compound H, as described herein, wherein the condition is selected from CNS disorders, treating drug addictions, and inflammatory conditions.

Other structures, methods, features, and advantages of the present disclosure will be, or become, apparent to one with skill in the art upon examination of the following drawings and detailed description. It is intended that all such additional structures, methods, features, and advantages be included within this description, be within the scope of the present disclosure, and be protected by the accompanying claims.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIG. 1.1 illustrates compounds of the present disclosure.
FIG. 1.2 illustrates compounds of the present disclosure.
FIG. 2.1 illustrates an exemplar reaction scheme.
FIG. 2.2 illustrates reaction scheme 1 in Example 1.
FIG. 2.3 illustrates reaction scheme 2 in Example 1.
FIG. 2.4 illustrates reaction scheme 3 in Example 1.
FIG. 2.5 illustrates reaction scheme 4 in Example 1.
FIG. 2.6 illustrates effects of methylation on binding are consistent with the effects on functional potency EC50 measured with oocytes.
FIG. 2.7 illustrates the initial reactions for synthesis of 2'-substituted nicotines.
FIG. 2.8 illustrates the alkylation of an imine intermediate of the 2'-cyanonicotine at the 2' position with appropriate Grignard reagents.

FIG. 2.9 illustrates the preparation of 2' aminoalkyl and carboxamido-nicotines from 2'-cyanonicotine.

FIG. 2.10 illustrates a comparison of 2' methyl-nicotine (■) with nicotine (●) in oocytes expressing α7 receptors. The methylated nicotine displays a 6.7-fold increase in potency at this nAChR relative to nicotine.

FIG. 2.11 illustrates a comparison of 5' Trans-Me-Nic (■) with 5' Cis-Me-Nic (♦) in oocytes expressing α7 receptors. The trans enantiomer activity is similar to nicotine on this receptor.

FIG. 2.12 illustrates a comparison of 5' Trans-Me-Nicotine (■) with 5' Cis-Me-Nicotine (♦) in oocytes expressing α4β2 receptors. Both the cis- and trans-enantiomers are inactive on α4β2 receptors.

FIG. 2.13 illustrates a comparison of 5' Trans-Me-Nic (■) with 5' Cis-Me-Nic (♦) in oocytes expressing α6/α3 chimera/β2 receptors. The alpha6beta2 receptor responds in an essentially identical manner to the two 5'-methyl nicotine enantiomers.

FIG. 3.1 illustrates the first step in the synthesis of 4-azetidinone precursor of methylated azetidinyl analogs of nicotine. The precursor can be commercially obtained in chiral forms where the 3-position of the propionyl group is (S)- or (R) form, leading to (S)- or (R) forms of the nicotine analog.

FIG. 3.2 illustrates the preparation of the N-methyl-azetidinone precursor in the synthesis of 3-(1,4-dimethyl-azetidin-2-yl)pyridine.

FIG. 3.3 illustrates the final step in the synthesis of a 4'-methylated azetidinyl analog of nicotine incorporating a methyl substituent equivalent to the 5'-methyl in nicotine that can affect nAChR selectivity.

FIG. 3.4 is a graph that illustrates the effects of trans-3-(1,4-dimethylazetidin-2-yl)pyridine (■) and cis-3-(1,4-dimethylazetidin-2-yl)pyridine (♦) on α4β2 receptors expressed in oocytes. The trans-diastereomers are significantly more potent than the cis-diastereomers, as in the 5'-methylnicotines.

FIG. 3.5 illustrates a methyl-azetidinone intermediate in the synthesis of the methyl azetidinyl analog of nicotine.

FIG. 4.1 illustrates the synthesis and separation of 3-(((2S,5R)-1,5-Dimethylpyrrolidine-2-yl)methoxy)-pyridine (Trans) and 3-(((2S,5S)-1,5-Dimethylpyrrolidine-2-yl)methoxy)pyridine (Cis).

FIG. 4.2 illustrates the starting reagent for synthesis of the methoxypyridine analogs of nicotine.

FIG. 4.3 illustrates the N-methylpyrrolidinone precursor.

FIG. 4.4 illustrate the intermediate in the synthesis of 3-(((2S,5R)-1,5-Dimethylpyrrolidine-2-yl)methoxy)-pyridine (Trans) and 3-(((2S,5S)-1,5-Dimethylpyrrolidine-2-yl)methoxy)pyridine (Cis).

FIG. 4.5 illustrates the synthesis and separation of 3-(((2S,5S)-1,5-Dimethylpyrrolidine-2-yl)methoxy)-pyridine (Trans enantiomer with low activity on alpha4beta2 receptors but high potency on alpha7 receptors).

FIG. 4.6 illustrates the synthesis and separation of 3-(((2S,5S)-1,5-Dimethylpyrrolidine-2-yl)methoxy)-pyridine (Cis enantiomer with low activity on alpha4beta2 and alpha7 receptors).

FIG. 4.7 illustrates both enantiomers, 3-(((2S,5R)-1,5-Dimethylpyrrolidine-2-byl)methoxy)pyridine (■) and 3-(((2S,5S)-1,5-Dimethylpyrrolidine-2-yl)methoxy)pyridine (♦) display essentially no agonistic activity on α4β2 receptors (n≥3) expressed in the *Xenopus* oocytes.

DETAILED DESCRIPTION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

DEFINITIONS

The term "substituted" refers to any one or more hydrogens on the designated atom or in a compound that can be replaced with a selection from the indicated group, provided that the designated atom's normal valence is not exceeded, and that the substitution results in a stable compound. The phrase " . . . a substituted or unsubstituted group selected from: an aliphatic group . . . " or a similar phrase means that each of the groups listed can be substituted or unsubstituted.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms.

As used herein, "alkenyl" or "alkenyl group" refers to an aliphatic hydrocarbon radical which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like. The term "lower alkenyl" means an alkyl group having less than 10 carbon atoms.

The term "alkynyl" refers to straight or branched chain hydrocarbon groups having 2 to 12 carbon atoms, preferably 2 to 4 carbon atoms, and at least one triple carbon to carbon bond, such as ethynyl. An alkynyl group is optionally substituted, unless stated otherwise, with one or more groups, selected from aryl (including substituted aryl), heteroaryl, heterocyclo (including substituted heterocyclo), carbocyclo (including substituted carbocyclo), halo, hydroxy, alkoxy (optionally substituted), aryloxy (optionally substituted), alkylester (optionally substituted), arylester (optionally substituted), alkanoyl (optionally substituted), aroyl (optionally substituted), cyano, nitro, amino, substituted amino, amido, lactam, urea, urethane, sulfonyl, and the like. The term "lower alkynyl" means an alkyl group having less than 10 carbon atoms.

The term "arylalkyl" refers to an arylalkyl group wherein the aryl and alkyl are as herein described. Examples of arylalkyl include, but are not limited to, -phenylmethyl, -phenylethyl, -phenylpropyl, -phenylbutyl, and -phenylpentyl.

The term "substituted," as in "substituted alkyl", "substituted cycloalkyl," "substituted cycloalkenyl," substituted aryl," substituted biaryl," "substituted fused aryl" and the like means that the substituted group may contain in place of one or more hydrogens a group such as hydroxy, amino, halo, trifluoromethyl, cyano, —NH (lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. The term "lower alkoxy" means an alkoxy group having less than 10 carbon atoms.

The term "cycloalkyl" refers to a non-aromatic mono-or multicyclic ring system of about 3 to about 10 carbon atoms, preferably of about 5 to about 10 carbon atoms. Preferred ring sizes of rings of the ring system include about 5 to about 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1-or 2-)yl, and the like.

The term "cycloalkenyl" refers to a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. Exemplary monocyclic cycloalkenyl include cyclopentenyl, cyclohexenyl, cycloheptenyl, and the like. An exemplary multicyclic cycloalkenyl is norbornylenyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

The term "biaryl" refers to an aryl, as defined above, where two aryl groups are joined by a direct bond or through an intervening alkyl group, preferably a lower alkyl group.

The term "fused aryl" refers to a multicyclic ring system as included in the term "aryl," and includes aryl groups and heteroaryl groups that are condensed. Examples are naphthyl, anthryl and phenanthryl. The bonds can be attached to any of the rings.

"Aralkyl" and "heteroaralkyl" refer to aryl and heteroaryl moieties, respectively, that are linked to a main structure by an intervening alkyl group, e.g., containing one or more methylene groups.

The term "fluorobenzyl" refers to a benzyl group wherein the phenyl moiety is substituted with one or more fluorine atoms, including 2, 3, 4 and 5 fluorine atom substituents.

Similarly, "halobenzyl" refers to benzyl substituted with one or more different halogens, including fluorine, chlorine, bromine, and iodine (not astatine).

The terms "sulfide" and "thioether" as used herein, alone or in combination, refer to a sulfur atom covalently linked to two atoms; the formal oxidation state of said sulfur is (II). These terms may be used interchangeably.

The term "sulfanyl" as used herein, alone or in combination, refers to the —S—R group, wherein R may be a group such as: alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. Non-limiting examples of sulfanyl groups include methylsulfanyl (—SCH$_3$) and iso-propylsulfanyl (—SCH(CH$_3$)$_2$) and the like.

The term "sulfoxide" as used herein, alone or in combination, refers to a sulfur atom covalently linked to three atoms, at least one of which is an oxygen atom; the formal oxidation state of said sulfur atom is (IV).

The term "sulfinyl" as used herein, alone or in combination, refers to the groups —S(O)—R, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. A non-limiting example of a sulfinyl group includes methylsulfinyl (—S(O)CH$_3$) and the like.

The term "sulfone" as used herein, alone or in combination, refers to a sulfur atom covalently linked to four atoms, at least two of which are oxygen atoms; the formal oxidation state of said sulfur atom is (VI).

The term "sulfonyl" as used herein, alone or in combination, refers to the groups —S(O$_2$)—R, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. A non-limiting example of a sulfonyl group includes methylsulfonyl (—S(O$_2$)CH$_3$) and the like.

The term "phosphate" as used herein, alone or in combination, refers to a phosphorus atom covalently linked to three carbon atoms, wherein the formal oxidation state of said phosphorus is (III).

The term "phosphinyl" as used herein, alone or in combination, refers to the monoradical derived from a phosphite group, as defined above.

The term "phosphonate" as used herein, alone or in combination, refers to a phosphorus atom covalently linked to four atoms, three of which are oxygen and one of which is carbon wherein the formal oxidation state of said phosphorus is (V).

The term "phosphonyl" as used herein, alone or in combination, refers to the monoradical derived from a phosphonate group, as defined above.

The term "phosphate" as used herein, alone or in combination, refers to a phosphorus atom covalently linked to four oxygen atoms, wherein the formal oxidation state of said phosphorus is (V).

The term "phosphatidyl" as used herein, alone or in combination, refers to the monoradical derived from a phosphate group, as defined above.

The terms ketone, ester, ether, and acyl have their art recognized meanings.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salts" refers to a compound of the present disclosure that can be modified by making acid or base salts thereof. Pharmaceutically acceptable salt refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. Examples of pharmaceutically acceptable salts include, but are not limited to, mineral or organic acid salts of basic residues such as amines; and alkali or organic salts of acidic residues such as carboxylic acids.

In the event that embodiments of the present disclosure form salts, these salts are within the scope of the present disclosure. Reference to an agent of any of the formulas herein is understood to include reference to salts thereof, unless otherwise indicated. The term "salt(s)", as employed herein, denotes acidic and/or basic salts formed with inorganic and/or organic acids and bases. In addition, when an agent contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of an agent may be formed, for example, by reacting the agent with an amount of acid or base, such as an equivalent amount, in a medium such as one in which the salt precipitates or in an aqueous medium followed by lyophilization.

Embodiments of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the agents that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

As used herein, "agent", "active agent", "inhibitor" or the like, can include a compound of the present disclosure or in some instances can refer to a separate drug or biological agent distinct from compounds described herein (such as in a combination of a compound of the disclosure and a drug). The agent or inhibitor can be disposed in a composition or a pharmaceutical composition.

As used herein, "treat", "treatment", "treating", and the like refer to acting upon a disease or disorder with an agent to affect the disease or disorder by improving or altering it. The improvement or alteration may include an improvement in symptoms or an alteration in the physiologic pathways associated with the disease or disorder. "Treatment," as used herein, covers one or more treatments of a disease in a host (e.g., a mammal, typically a human or non-human animal of veterinary interest), and includes: CNS disorders (e.g., schizophrenia, Alzheimer's disease, Parkinson's disease, attention-deficit-hyperactivity disorder), treating drug addictions (e.g., smoking and alcoholism) and controlling inflammatory conditions (e.g., sepsis, acute pancreatitis, rheumatoid arthritis).

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a disease or symptom thereof and/or may be therapeutic in terms of a partial or complete cure for a disease and/or adverse effect attributable to the disease.

The terms "activate" and "activation" can refer to a response from acting upon a biological target with a compound of the present disclosure.

As used herein, "pharmaceutical composition" refers to the combination of an active agent with a pharmaceutically acceptable carrier. As used herein, a "pharmaceutical composition" refers to a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

The term "isolated compound" refers to a compound which has been substantially separated from, or enriched relative to, other compounds with which it occurs in nature. Isolated compounds are usually at least about 80%, at least 90% pure, at least 98% pure, or at least about 99% pure, by weight. The present disclosure is meant to include diastereomers as well as their racemic and resolved, enantiomerically pure forms and pharmaceutically acceptable salts thereof.

The term "unit dosage form," as used herein, refers to physically discrete units suitable as unitary dosages for human and/or animal subjects, each unit containing a predetermined quantity of a compound calculated in an amount sufficient (e.g., weight of host, disease, severity of the disease, etc) to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the host.

The term "therapeutically effective amount" as used herein refers to that amount of an embodiment of the agent (which may be referred to as a compound) being administered that will relieve to some extent one or more of the symptoms of the disease being treated, and/or that amount that will prevent, to some extent, one or more of the symptoms of the disease that the host being treated has or is at risk of developing.

The term "prodrug" refers to a compound whose efficacy may be enhanced after a conversion step that occurs in vivo after administering the compound to a subject or patient. Typical examples of prodrugs include organic phosphates or esters of alcohols or thioalcohols. See Remington's Pharmaceutical Sciences, 16th Ed., A. Osol, Ed. (1980), the disclosure of which is incorporated by reference herein.

The term "pharmaceutically acceptable prodrugs" refers to those prodrugs of the compounds useful according to the present disclosure which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the disclosure. Functional groups that may be rapidly transformed, by metabolic cleavage, in vivo form a class of groups reactive with the carboxyl group of the compounds of this disclosure. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl-and triethysilyl), monoesters formed with dicarboxylic acids (such as succinyl), and the like. Because of the ease with which the metabolically cleavable groups of the compounds useful according to this disclosure are cleaved in vivo, the compounds bearing such groups act as pro-drugs. The compounds bearing the metabolically cleavable groups have the advantage that they may exhibit improved bioavailability and or better ease of administration as a result of enhanced solubility and/or rate of absorption conferred upon the parent compound by virtue of the presence of the metabolically cleavable group. Prodrugs can include compounds of the present disclosure wherein a hydroxy, amino, or sulthydryl group is bonded to any group that, when the prodrug of the present disclosure is administered to a mammalian subject, it cleaves to form a free hydroxyl, free amino, or free sulthydryl group, respectively. Examples of prodrugs include, but are not limited to acetate, formate and benzoate derivatives of alcohol and amine functional groups in the compounds of the present disclosure.

To the extent that the disclosed compounds, and salts thereof, may exist in their tautomeric form, all such tautomeric forms are contemplated herein as part of the present disclosure.

All stereoisomers of the compounds of the present disclosure, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations. In some embodiments, the stereoisomers are synthesized or separated from one another can thus can be claimed as a single stereoisomer (e.g., enantiomer, See scheme 1).

The term "administration" refers to introducing a compound of the present disclosure into a host. One preferred route of administration of the compound is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, the term "host," "subject," "patient," includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host noted above or another organism that is alive. The term "living host" refers to the entire host or organism and not just a part excised (e.g., a liver or other organ) from the living host.

Discussion

Embodiments of the present disclosure provide for compounds such as those shown in FIG. 1.1 (compounds A, B, C, and D), 2'substituted nicotine compounds, azetidine compounds, ether linked nicotine compounds (FIG. 1.2, compounds E, F, G, and H), methods of synthesis of the compounds, methods of treatment of a condition using the compounds, 2'substituted nicotine compounds, azetidine compounds, or ether linked nicotine compounds, methods of selectively stimulating alpha7 nAChR and/or alpha4beta2 receptors, and the like.

An embodiment of the disclosure notes that nicotine's structure can be manipulated by substitutions and shrinkage of the saturated ring such that alpha7-selective drugs can be obtained. Furthermore, in an embodiment, methylation of the saturated ring carbon bearing the 3-pyridyl group leads to the first nicotine analog, 2'-methylnicotine, that displays excellent agonist activity at both alpha4beta2 and alpha7 receptors; this offers a unique substance that can concurrently stimulate the cognitive pathways of the brain that is predicted to have a greater effect than would stimulation of either receptor alone.

Nicotine, the major active ingredient of tobacco, is a natural product that has been self-administered by humans for thousands of years. Chronic self-administration of tobacco products causes a serious life long addiction causes serious individual and public health problems. Recent research has demonstrated that nicotine and other nicotinic acetylcholine receptor (nAChR) agonists also can exert beneficial (therapeutic) actions, such as enhancing cognition, reducing anxiety, and treating inflammations. There are at least 15 different nAChRs in the mammalian organism. Each is composed of five polypeptide subunits; at least two of these must be alpha subunits, which constitute most of each acetylcholine (or nicotine) binding site. At least two molecules of agonist must bind to each receptor for significant activation. Since the procognitive actions are mediated by alpha7 (composed of five alpha7 subunits) and alpha4beta2 nAChR subtypes, compounds that stimulate one or both of these nAChR subtypes without stimulating other nAChRs are of great potential pharmaceutical and medical interest. Nicotinic stimulation at other nAChRs (including those found in autonomic ganglia, the intestinal nerve plexuses and the somatic neuromuscular junction) often causes deleterious adverse effects. Since nicotine stimulates all of these nAChRs, its therapeutic potential is limited.

Embodiments of the present disclosure describe new analogs of nicotine, in particular, compounds A-D in FIG. 1.1, 2' substituted nicotine compounds, azetidine compounds, and ether linked nicotine compounds (FIG. 1.2, compounds E, F, G, and H).

Embodiments of the present disclosure can include the synthesis of new analogs of nicotine (and of its 1-methyl-2-(3-pyridyl)-azetidinyl analog) that either selectively stimulate the alpha7 nAChR alone, or selectively stimulate both alpha4beta2 as well as alpha7 nAChRs. These could be useful drugs for enhancing cognition in CNS disorders (e.g., schizophrenia, Alzheimer's disease, Parkinson's disease, attention-deficit-hyperactivity disorder), treating drug addictions (e.g., smoking and alcoholism), and controlling inflammatory conditions (e.g., sepsis, acute pancreatitis, and rheumatoid arthritis).

Embodiments of the present disclosure describe new analogs of nicotine (See FIG. 1.1, compounds A-D, (substitution for the 4', 5', 6', and 7', trans positions)) that, unexpectedly and for the first time, selectively stimulate alpha7 nAChRs, and thus avoid adverse effects mediated through other nAChRs. Embodiments of the present disclosure also provide methods for preparing new analogs of nicotine (and of its closely related 4-, 6- and 7-membered saturated ring analogs) that can simultaneously stimulate both alpha7 receptors and alpha4beta2subtype nAChRs to produce even greater procognitive therapeutic effect than would be obtained by selectively stimulating only one of these receptors.

While investigating the relationship between nicotine's structure and its effects on the two pro-cognitive nAChRs, it was discovered that certain key sites on the nicotine molecule control its ability to potently activate either the alpha7 or the alpha4beta2 nAChR. It has been demonstrated in this disclosure and for the first time that adding an alkyl group or other substituents at these sites can greatly enhance potency, selectivity, and efficacy at alpha7 nAChRs.

In particular, this disclosure illustrates that placement of a substituent at the 5' trans position of (S)-nicotine (or the corresponding 4'-, 6'- and 7'-trans positions in the 4-, 6- and 7-membered saturated ring analogs of nicotine) (See FIG. 1.1, compounds A, B, C, and D, described below (substitution for the 4', 5', 6', and 7' trans positions and not the 2' position)), prevents its interaction with alpha4beta2 nAChRs without detrimental effects on the ability of the nicotine analog to stimulate the alpha7 nAChR.

An embodiment of the disclosure also describes two different methods for the synthesis of a variety of 2'substituted nicotines (and the corresponding 4-, 6- and 7-membered saturated ring analogs of nicotine) (See FIG. 1.1, compounds A, B, C, and D, described below substitution for the 2' position and not the 4', 5', 6', and 7' positions)). A method for the synthesis of 2'substituted nicotines does not appear to have been previously reported in the scientific or patent literature. An embodiment of the synthetic procedure for obtaining racemic 2'substituted nicotines is described in the Examples. The present disclosure also illustrates that the two enantiomers from each racemic product can be obtained by chiral HPLC and that the enantiomers corresponding to (S)-nicotine have superior potency for the two procognitive nAChRs. In addition, a method for asymmetric synthesis of 2'substituted nicotines and their congeners is described.

An embodiment of this disclosure demonstrates that placement of a small substituent at the 2' site on the nicotine molecule enhances affinity for the two procognitive nAChRs. This substitution is particularly significant for improving potency at the alpha7 nAChR. So nicotine analogs can now be synthesized that are potent selective agonists at alpha7 receptors by introducing substituents at both the 5' (and the corresponding 4-, 6- and 7-membered saturated ring analogs of nicotine) and/or the 2' atoms of nicotine.

Schizophrenia is one disease therapy that can benefit from such a drug. Schizophrenics do not express sufficient numbers of alpha7 receptors and this may explain their relative inability to filter out unwanted repetitive sensory stimuli. A high percentage (83%) of schizophrenics smoke extensively, probably to fully stimulate their alpha7 receptors. Since alpha7 receptors are at least 50× less sensitive to nicotine relative to alpha4beta2 nAChRs, these people attempt to achieve higher brain concentrations of nicotine to self-treat their sensory system deficits. (Martin et al., 2004). Schizophrenics generally display impaired ability to filter repetitive auditory and visual stimuli and alpha7 and alpha4beta2 agonists can improve sensory gating in a mouse model (Stevens et al., 1998; Wildeboer and Stevens, 2011).

Compounds that simultaneously stimulate both alpha7 and alpha4beta2 receptors may be desirable for treating certain diseases. In this case, addition of a 2' methyl nicotine substituent (but not a 5' substituent or optionally the 5') would enhance potency at both nAChRs. Recent clinical tests have shown that selective stimulation of either alpha4beta2 or alpha7 receptors produce weak improvements in cognition in AD and ADHD patients. Since these receptors are not always expressed together in the same cell or synapse and each subtype may affect different signaling pathways or different parts of the same pathway, simultaneous stimulation of both receptors is likely to produce more significant therapeutic improvements in cognition in these diseases.

Racemic 1-methyl-2-(3-pyridyl)-azetidine has been synthesized and was used for several years as a PET imaging agent for detecting changes in alpha4beta2 receptor expression in the living human brain in certain neurodegenerative diseases. However, the two enantiomeric forms have never been isolated from this racemate, synthesized separately or pharmacologically analyzed separately. An embodiment of the present disclosure illustrates a method for the total synthesis of either enantiomer using a known asymmetric reagent and a new method (conditions) for reducing the azetidinone intermediate to the azetidine. Use of the method permitted showed that the (S)-enantiomer analogs of nicotine and nornicotine possesses exceptional ability to interact with the procognitive nAChRs. Scheme 1 (below in the detailed description) illustrates these synthesis methods and also indicates how substitutions on the ring carbons next to the azetidinyl N that are equivalent to the 2' and 5' sites of the nicotine pyrrolidinyl ring can be added to obtain potent nicotinic agonists. In an embodiment, one or more of the hydrogens on each of the rings can be substituted with an R (e.g., RP1 to RP6, RN1, and R2', R4', and R5') group as described herein and consistent with the reaction sequence described in Scheme 1.

Scheme 1: A new synthesis of azetidinyl analogs of nicotine (The 2' asymmetric carbon is only shown in compound 1).

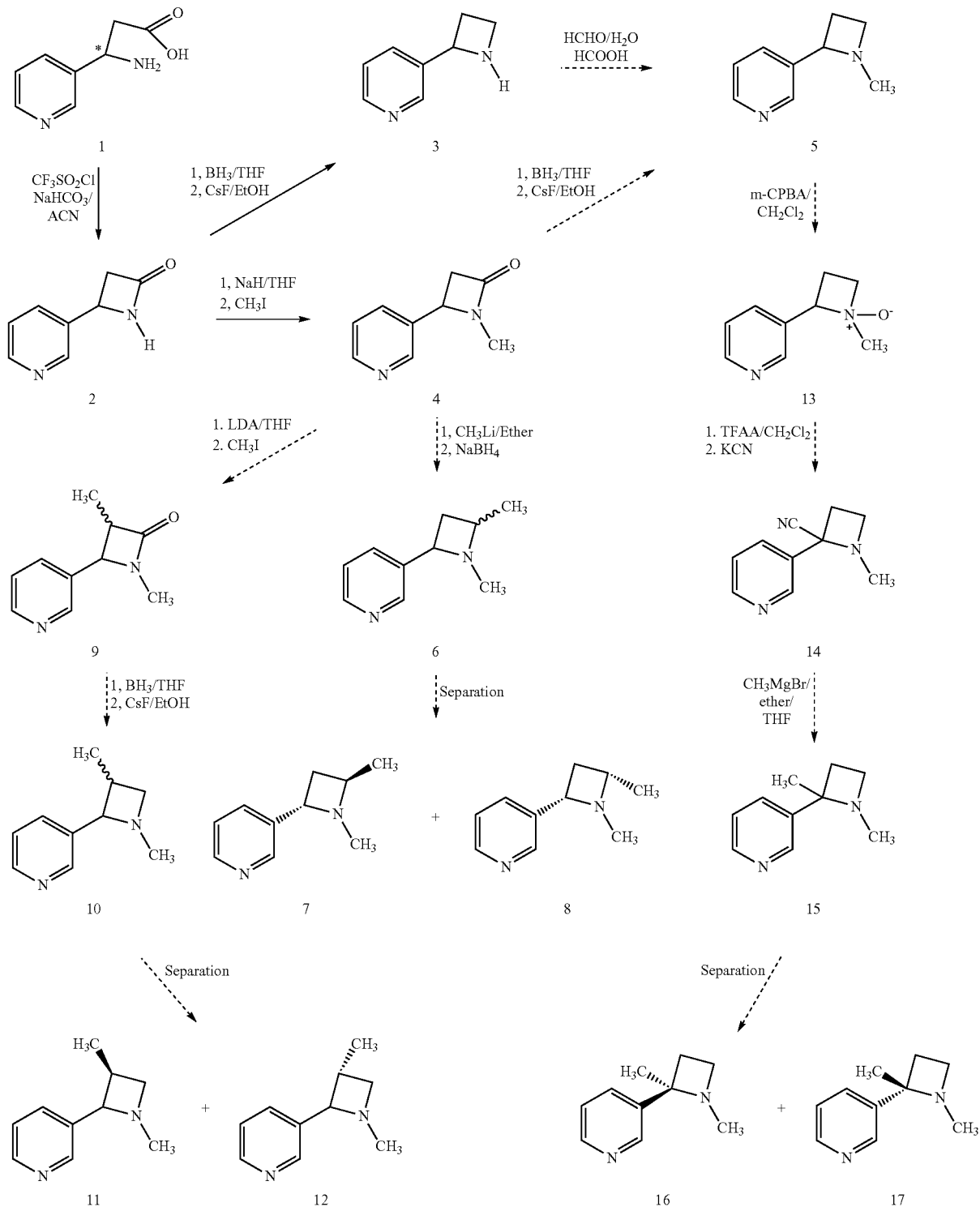

Additional details regarding the synthesis of four-membered (azetidinyl) analogs containing substituents favoring alpha7 nAChR stimulation are shown in Example 3.

Racemic dl-2-(pyridin-3-yl)azetidine (dl-3) was first synthesized by Secor and Edwards (1979) from pyridine-3-carboxaldehyde via a seven step reaction sequence. They also prepared its N-methyl derivative (dl-5), the nicotine homolog, and examined some of the pharmacological activities of these compounds. The methods of synthesis for the 6- and 7-membered ring analogs are in the literature.

In addition, other nicotinoid compounds have been prepared and tested that possess 5'-methyl-pyrrolidinyl or the analogous 4' methyl-azetidinyl rings attached either directly to a pyridyl ring at its 3 position or indirectly by a linking methylene-ether oxygen-methylene group to show that alpha7 nAChR selectivity can be increased with respect to alpha4beta2 (binding and agonism) nAChRs in all these cases by having the 5' methyl group situated trans- with respect to the 2'-connection by way of the linker group to the 3-pyridine. In an embodiment, the nicotinoid compounds include trans- and cis-alkylated saturated N-containing ring compounds containing a linking moiety between the saturated ring and the aromatic ring (e.g., pyridyl), where the site of alkylation is a carbon adjacent to the N. The nicotinoid compounds would include the 2' position as well as the distant adjacent C, which is 4'(azetidinyl ring), 5'(pyrrolidinyl ring), 6' (piperidinyl ring) or 7'(azepinyl ring) (See FIG. 1.2). FIG. 1.2 illustrates compounds E, F, G, and H that includes the described above, where the alkyl (e.g., methyl group) (in R4', R5', R6' or R7' position, respectively), for example, may be situated trans- with respect to the 2'-connection. In addition, the methyl group can be substituted for another group defined below for in R4', R5', R6' or R7'.

An embodiment of the present disclosure describes a new synthesis of the pyridylazetidine analogs, which can be asymmetric, providing only (S) or (R) enantiomers (Scheme 1). The commercially available dl-3-amino-3-(pyridin-3-yl) propionic acid (dl-1) is cyclized with trifluoromethylsulfonyl chloride in acetonitrile solution (trifluoromethanesulfonyl chloride or methanesulfonylchloride in acetonitrile can alternately be used) in the presence of sodium bicarbonate (or potassium bicarbonate) (a similar method was developed for the preparation of dl-4-phenylazetidin-2-one by Loewe et al. 1991) to dl-4-(pyridin-3-yl)azetidin-2-one (dl-2) and its lactone moiety was reduced with borane-tetrahydrofuran complex and treatment with cesium fluoride (alternately reduction with lithium aluminum hydride in diethylether) by a procedure similar to that of Lin at al. (1994), who used cotinine derivatives, furnishing the dl-2-(pyridin-3-yeazetidine (dl-3). The N-methyl derivative (dl-5) was prepared by the Eschweiler-Clarke procedure and from 1-methyl-4-(pyridin-3-yl)azetidin-2-one (dl-4) with the above mentioned borane reduction. Compound dl-4 was prepared from dl-4-(pyridin-3-yl)azetidin-2-one (dl-2) by methylation of its N-sodium salt with methyl iodide (alternately one can prepare other N-alkyl analogs using the appropriate alkyl halogenide) using the method of van Henegouwen at al. (2000) for the N-methylation of lactams. Compound dl-4, the trans- and cis-1,4-dimethyl-2-(pyridin-3-yl)azetidine (dl-7 and dl-8 respectively) was prepared by reaction with methyl lithium (or other alkyl lithiums to prepare other C-alkyl analogs) followed by sodium borohydride reduction and chromatographic separation of the isomers according to the analog reaction in the nicotine series (Shibagaki et al. 1986). The trans- and cis-1,3-dimethyl-2-(pyridin-3-yl)azetidine (dl-11 and dl-12 respectively) were prepared by starting from compound dl-4 by alpha methylation on the N-methyl lactam ring by lithium diisopropyl amide, methyl iodide (other C-alkyl derivatives can be prepared using appropriate alkyl lithiums) and with subsequent reduction by boran-tetrahyrdofuran complex and separation of the isomers, which procedure we used successfully earlier in the case of cotinine according to Lin at al. (1994). We prepare the 2-methylated analogon (dl-15) using our developed procedure for the nicotine series (Rouchaud and Kem, 2010) by N-oxidation of compound dl-5 with m-chloro-peroxybenzoic acid (or alternately peroxybenzoic acid) followed by iminium formation and reaction with cyanide ion and finished with cyano-methyl exchange with methyl magnesium bromide (or other methyl Grignard reagents).

Since the enantiomers of our starting material, the 3-amino-3-(pyridin-3-yl)propionic acid with known absolute configuration, are commercially available from many companies, it is possible to therefore repeat the above described reactions using (R)- or (S)-3-amino-3-(pyridin-3-yl)propionic acid, which will yield the above mentioned target compounds in pure enantiomeric form with known absolute configuration, using the above mentioned reaction sequences. In the case of compound dl-15 we use chiral separation to get its (R)- and (S)-enantiomers.

Also 2-(pyridine-3-yl)azetidines are prepared in which the pyridine ring has alkyl or other substituents, alone or in addition to substituents on the saturated ring as described above. The starting materials, 3-amino-3-(methylpyridin-3-yl)propionic acids, are commercially available or can be prepared using one of several known methods for the synthesis 3-amino-3-(pyridine-3-yl)propionic acid. Throughout the above description of compound syntheses, where we mention "methyl" we also can introduce other lower-alkyl group substituents that may also contain amino, hydroxylic or other groups.

The method for asymmetric synthesis of the azetidinyl analogs of nicotine shown in scheme 1 can also be used for the asymmetric synthesis of the 2'-substituted nicotines, as shown in Scheme 2 below. In an embodiment, one or more of the hydrogens on each of the rings can be substituted with an R (e.g., RP1 to RP6, RN1, and R2', R4', and R5') group as described herein and consistent with the reaction sequence described in Scheme 2.

Scheme 2: Proposed method for asymmetric synthesis of 2'-alkyl-nicotines and other nicotine analogs

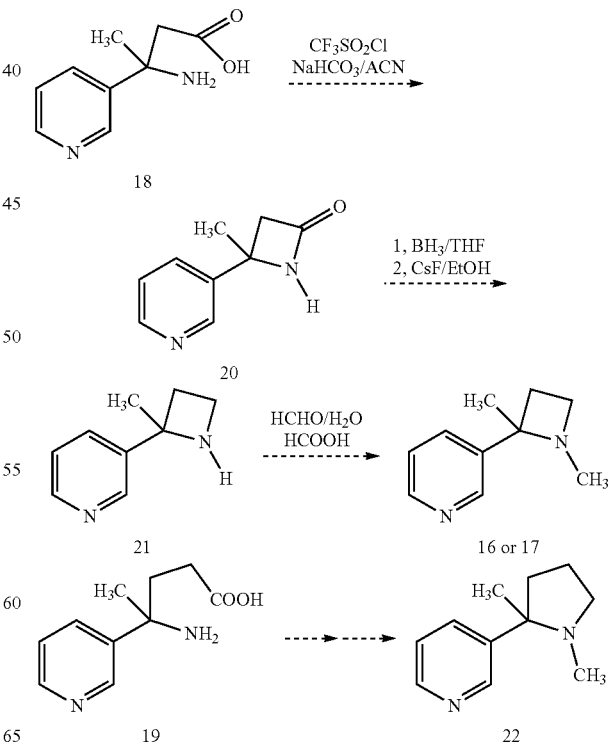

REFERENCES FOR SYNTHETIC METHODS, EACH OF WHICH IS INCORPORATED HEREIN BY REFERENCE

Loewe, M. F., Cvetovich, R. J. and Hazen, G. G. (1991). An efficient beta-amino acid cyclodehydratation using mathanesulfonyl chloride to thienamycin intermediate 3-(1-hydroxyethyl)-4-(methoxycarbonylmethyl)-azetidin-2-one. Tetrahedron Letters 32, 2299-2302.

van Henegouwen, W. G., Fieseler, R. M., Rutjes, F. P. J. T. and Hiemstra, H. (2000). First Total Synthesis of ent-Gelsedine via a Novel Iodide-Promoted Allene N-acyliminium Ion Cyclization. Journal of Organic Chemistry 65, 8317-8325.

Lin, N-H., Carrera, G. M. Jr. and Anderson, D. J. (1994). Synthesis and Evaluation of Nicotine Analogs as Neuronal Nicotinic Acetylcholine Receptor Ligands. Journal of Medicinal Chemistry 37, 3542-3553.

Rouchaud, A. and Kem, W. R. (2010). Racemic synthesis of 2'-substituted nicotine analogs. Journal of Heterocyclic Chemistry. (Submitted).

Secor, H. V. and Edwards, W. B. III. (1979). Nicotine Analogs: Synthesis of Pyridylazetidines. Journal of Organic Chemistry 44, 3136-3140.

Shibagaki, M., Matsushita, H. and Kaneko, H. (1986). The Synthesis of 5'-Alkylnicotines. Heterocycles 24, 423-428 and 2315-2319.

Compounds

FIG. 1.1 and FIG. 1.2 illustrate compounds A, B, C, and D and E, F, G, and H, respectively. In an embodiment, in each of compounds A, B, C, and D and E, F, G, and H, R2' and R4', R5', R6', and R7', respectively (R2' and R4', R2' and R5', etc), can each be independently substituted with a group such as an alkyl group (e.g., having 1 to 6 carbons or 1 or 2 carbons), an alkyl amino group having 1 to 6 carbons (e.g., or 1 or 2 carbons), an alkyl group having a hydroxylic group and having from 1 to 6 carbons (e.g., or 1 or 2 carbons), and a methoxy group. In an embodiment, R2' and the R4', R5', R6', and R7', respectively, can each be independently substituted with methyl, ethyl, n-Pr, $CH_2NH_2$, $CH_2OH$, or $CONH_2$. Each of RN1, RP1, RP2, RP3, RP4, RP5, RP6, RP7, and RP8 can each be independently selected from a substituted or an unsubstituted group selected from: an aliphatic group, an alkoxy group, a cycloalkyl group, an aryl group, a heteroaryl group, and a heterocyclic group.

In an embodiment of compounds A and E, R4' is at the trans position to the substituent at position 2' and is a group such as an alkyl group (e.g., having from 1 to 6 carbons or 1 or 2 carbons), an alkyl amino group having from 1 to 6 carbons (e.g., or 1 or 2 carbons), an alkyl group having a hydroxylic group and having from 1 to 6 carbons (e.g., or 1 or 2 carbons), and a methoxy group. In an embodiment the alkyl group is a methyl group or an ethyl group. In an embodiment, R4' can be substituted with methyl, ethyl, n-Pr, $CH_2NH_2$, $CH_2OH$, or $CONH_2$. R2' is a substituted or unsubstituted group selected from: an aliphatic group, an alkoxy group, a cycloalkyl group, an aryl group, a heteroaryl group, and a heterocyclic group. Each of RN1, RP1, RP2, RP3, RP4 and RP5 are independently a substituted or unsubstituted group selected from: an aliphatic group, an alkoxy group, a cycloalkyl group, an aryl group, a heteroaryl group, and a heterocyclic group. In an alternative embodiment, R4' is at the cis position.

In an embodiment of compounds B and F, R5' is at the trans position to the substituent at position 2' and is a group such as an alkyl group (e.g., having from 1 to 6 carbons or 1 or 2 carbons), an alkyl amino group having from 1 to 6 carbons (e.g., or 1 or 2 carbons), an alkyl group having a hydroxylic group and having from 1 to 6 carbons (e.g., or 1 or 2 carbons), and a methoxy group. In an embodiment the alkyl group is a methyl group or an ethyl group. In an embodiment, R5' can be substituted with methyl, ethyl, n-Pr, $CH_2NH_2$, $CH_2OH$, or $CONH_2$. R2' is a substituted or unsubstituted group selected from: an aliphatic group, an alkoxy group, a cycloalkyl group, an aryl group, a heteroaryl group, and a heterocyclic group. Each of RN1, RP1, RP2, RP3, RP4, RP5, and RP6 are independently a substituted or unsubstituted group selected from: an aliphatic group, an alkoxy group, a cycloalkyl group, an aryl group, a heteroaryl group, and a heterocyclic group. In an alternative embodiment, R5' is at the cis position.

In an embodiment of compounds C and G, R6' is at the trans position to the substituent at position 2' and is a group such as an alkyl group (e.g., having from 1 to 6 carbons or 1 or 2 carbons), an alkyl amino group having from 1 to 6 carbons (e.g., having from 1 to 6 carbons or 1 or 2 carbons), an alkyl group having a hydroxylic group and having from 1 to 6 carbons (e.g., having from 1 to 6 carbons or 1 or 2 carbons), and a methoxy group. In an embodiment the alkyl group is a methyl group or an ethyl group. In an embodiment, R6' can be substituted with methyl, ethyl, n-Pr, $CH_2NH_2$, $CH_2OH$, or $CONH_2$. R2' is a substituted or unsubstituted group selected from: an aliphatic group, an alkoxy group, a cycloalkyl group, an aryl group, a heteroaryl group, and a heterocyclic group. Each of RN1, RP1, RP2, RP3, RP4, RP5, RP6, and RP7, are independently a substituted or unsubstituted group selected from: an aliphatic group, an alkoxy group, a cycloalkyl group, an aryl group, a heteroaryl group, and a heterocyclic group. In an alternative embodiment, R6' is at the cis position.

In an embodiment of compounds D and H, R7' is at the trans position to the substituent at position 2' and is a group such as an alkyl group (e.g., having from 1 to 6 carbons or 1 or 2 carbons), an alkyl amino group having from 1 to 6 carbons (e.g., or 1 or 2 carbons), an alkyl group having a hydroxylic group and having from 1 to 6 carbons (e.g., or 1 or 2 carbons), and a methoxy group. In an embodiment the alkyl group is a methyl group or an ethyl group. In an embodiment, R7' can be substituted with methyl, ethyl, n-Pr, $CH_2NH_2$, $CH_2OH$, or $CONH_2$. R2' is a substituted or unsubstituted group selected from: an aliphatic group, an alkoxy group, a cycloalkyl group, an aryl group, a heteroaryl group, and a heterocyclic group. Each of RN1, RP1, RP2, RP3, RP4, RP5, RP6, RP7, and RP8 are independently a substituted or unsubstituted group selected from: an aliphatic group, an alkoxy group, a cycloalkyl group, an aryl group, a heteroaryl group, and a heterocyclic group. In an alternative embodiment, R7' is at the cis position.

In an embodiment of compounds A and E, R2' is a group such as an alkyl group (e.g., having from 1 to 6 carbons or 1 or 2 carbons), an alkyl amino group having from 1 to 6 carbons (e.g., or 1 or 2 carbons), an alkyl group having a hydroxylic group and having from 1 to 6 carbons (e.g., or 1 or 2 carbons), and a methoxy group. In an embodiment the alkyl group is a methyl group or an ethyl group. In an embodiment, R2' can be substituted with methyl, ethyl, n-Pr, $CH_2NH_2$, $CH_2OH$, or $CONH_2$. R4' is a substituted or unsubstituted group selected from: an aliphatic group, an alkoxy group, a cycloalkyl group, an aryl group, a heteroaryl group, and a heterocyclic group. Each of RN1, RP1, RP2, RP3, RP4 and RP5 are independently a substituted or unsubstituted group selected from: an aliphatic group, an alkoxy group, a cycloalkyl group, an aryl group, a heteroaryl group, and a heterocyclic group. In an alternative embodiment, R2' is at the cis position or is in the trans position, to the substituent at position R4'.

In an embodiment of compounds B and F, R2' is a group such as an alkyl group (e.g., having from 1 to 6 carbons or 1 or 2 carbons), an alkyl amino group having from 1 to 6 carbons (e.g., having from 1 to 6 carbons or 1 or 2 carbons), an alkyl group having a hydroxylic group and having from 1 to 6 carbons (e.g., or 1 or 2 carbons), and a methoxy group. In an embodiment the alkyl group is a methyl group or an ethyl group. In an embodiment, R2' can be substituted with methyl, ethyl, n-Pr, $CH_2NH_2$, $CH_2OH$, or $CONH_2$. R5' is a substituted or unsubstituted group selected from: an aliphatic group, an alkoxy group, a cycloalkyl group, an aryl group, a heteroaryl group, and a heterocyclic group. Each of RN1, RP1, RP2, RP3, RP4, RP5, and RP6 are independently a substituted or unsubstituted group selected from: an aliphatic group, an alkoxy group, a cycloalkyl group, an aryl group, a heteroaryl group, and a heterocyclic group. In an alternative embodiment, R2' is at the cis position or is in the trans position, to the substituent at position R5'.

In an embodiment of compounds C and G, R2' is a group such as an alkyl group (e.g., having from 1 to 6 carbons or 1 or 2 carbons), an alkyl amino group having from 1 to 6 carbons (e.g., having from 1 to 6 carbons or 1 or 2 carbons), an alkyl group having a hydroxylic group and having from 1 to 6 carbons (e.g., or 1 or 2 carbons), and a methoxy group. In an embodiment the alkyl group is a methyl group or an ethyl group. In an embodiment, R2' can be substituted with methyl, ethyl, n-Pr, $CH_2NH_2$, $CH_2OH$, or $CONH_2$. R6' is a substituted or unsubstituted group selected from: an aliphatic group, an alkoxy group, a cycloalkyl group, an aryl group, a heteroaryl group, and a heterocyclic group. Each of RN1, RP1, RP2, RP3, RP4, RP5, RP6, and RP7 are independently a substituted or unsubstituted group selected from: an aliphatic group, an alkoxy group, a cycloalkyl group, an aryl group, a heteroaryl group, and a heterocyclic group. In an alternative embodiment, R2' is at the cis position or is in the trans position, to the substituent at position R6'.

In an embodiment of compounds D and H, R2' is a group such as an alkyl group (e.g., having from 1 to 6 carbons or 1 or 2 carbons), an alkyl amino group having from 1 to 6 carbons (e.g., or 1 or 2 carbons), an alkyl group having a hydroxylic group and having from 1 to 6 carbons (e.g., or 1 or 2 carbons), and a methoxy group. In an embodiment the alkyl group is a methyl group or an ethyl group. In an embodiment, R2' can be substituted with methyl, ethyl, n-Pr, $CH_2NH_2$, $CH_2OH$, or $CONH_2$. R7' is a substituted or unsubstituted group selected from: an aliphatic group, an alkoxy group, a cycloalkyl group, an aryl group, a heteroaryl group, and a heterocyclic group. Each of RN1, RP1, RP2, RP3, RP4, RP5, RP6, RP7, and RP8 are independently a substituted or unsubstituted group selected from: an aliphatic group, an alkoxy group, a cycloalkyl group, an aryl group, a heteroaryl group, and a heterocyclic group. In an alternative embodiment, R2' is at the cis position or is in the trans position, to the substituent at position R7'.

In an embodiment, any one of compounds A-D and E-H described herein can be in a pharmaceutically composition in a therapeutically effective amount to achieved the desired results. In an embodiment, any one of compounds A-D and E-H described herein can be in the form of a pharmaceutically acceptable salt. In an embodiment, any one of compounds A-D and E-H described herein can be in the form of a pharmaceutically acceptable prodrug. In an embodiment, an atropisomer, a racemic mixture, and/or a stereoisomer, of any one of compounds A-D and E-H described herein are contemplated to be disclosed by the present disclosure.

Pharmaceutical Compositions

Administration of the active compounds (e.g., compounds noted in FIG. 1.1 and the related discussion and elsewhere in the application such as compounds A, B, C, D, 2'substituted nicotine compounds, azetidine compounds, and ether linked nicotine compounds (FIG. 1.2, compounds E, F, G, and H) and salts described herein can be via any of the accepted modes of administration for therapeutic agents. These methods include oral, parenteral, transdermal, subcutaneous and other systemic modes. In some instances it may be necessary to administer the composition parenterally.

Depending on the intended mode, the compositions may be in the form of solid, semisolid or liquid dosage forms, such as, for example, tablets, suppositories, pills, capsules, powders, liquids, suspensions, skin patch, or the like, preferably in unit dosage forms suitable for single administration of precise dosages. The compositions can include a conventional pharmaceutical excipient and an active compound of the present disclosure or the pharmaceutically acceptable salts thereof (e.g., compounds noted in FIGS. 1.1 and 1.2, and 2' substituted nicotine compounds, azetidine compounds, and ether linked nicotine compounds, and elsewhere in the application) and, in addition, may include other medicinal agents, pharmaceutical agents, carriers, adjuvants, diluents, etc.

Embodiments of the compounds of the present disclosure are typically administered to a patient in the form of a pharmaceutical composition or formulation. Such pharmaceutical compositions can be administered to the patient by any acceptable route of administration including, but not limited to, oral, rectal, vaginal, nasal, inhaled, topical (including transdermal) and parenteral modes of administration.

Accordingly, an embodiment of the present disclosure is directed to a pharmaceutical composition comprising a pharmaceutically-acceptable carrier or excipient and a therapeutically effective amount of a compound of the present disclosure or a pharmaceutically acceptable salt thereof. Optionally, such pharmaceutical compositions may contain other therapeutic and/or formulating agents if desired. When discussing compositions, the "compound of the present disclosure" may also be referred to herein as the "active agent" or "agent". As used herein, the term "compound of the present disclosure" is intended to include a novel compound described in formulae provided herein and in the claims (e.g., compounds noted in FIG. 1.1 FIGS. 1.1 and 1.2, and 2' substituted nicotine compounds, azetidine compounds, and ether linked nicotine compounds, and elsewhere in the application).

The pharmaceutical compositions of the present disclosure typically contain a therapeutically effective amount of a compound of the present disclosure or a pharmaceutically-acceptable salt thereof. Typically, such pharmaceutical compositions can contain about 0.1 to about 95% by weight of the active agent; preferably, about 5 to about 70% by weight; and more preferably about 10 to about 60% by weight of the active agent.

A conventional carrier or excipient can be used in the pharmaceutical compositions of the present disclosure. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this present disclosure are commercially-available. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the present disclosure are preferably packaged in a unit dosage form. The term "unit dosage form" refers to a physically discrete unit suitable for dosing a patient, e.g., each unit containing a predetermined quantity of active agent (e.g., compounds A, B, C, and D and E, F, G, and H) calculated to produce the desired therapeutic effect either alone or in combination with one or more additional units. For example, such unit dosage forms can be capsules, tablets, pills, and the like, or unit packages suitable for parenteral administration.

In an embodiment, the pharmaceutical compositions of the present disclosure are suitable for oral administration. Suitable pharmaceutical compositions for oral administration can be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present disclosure as an active ingredient.

When intended for oral administration in a solid dosage form (i.e., as capsules, tablets, pills and the like), the pharmaceutical compositions of the present disclosure can typically include the active agent and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the present disclosure. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like.

Pharmaceutical compositions of the present disclosure may also be formulated to provide slow or controlled release of the active agent using, by way of example, hydroxypropyl methyl cellulose in varying proportions; or other polymer matrices, liposomes and/or microspheres. In addition, the pharmaceutical compositions of the present disclosure may optionally contain opacifying agents and can be formulated so that they release the active ingredient only, or preferentially, in a certain portion of the gastrointestinal tract, optionally, in a delayed manner. Examples of embedding compositions which can be used include polymeric substances and waxes. The active agent can also be in microencapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The compounds of the present disclosure can also be administered parenterally (e.g., by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations can be rendered sterile by use of a sterile injectable medium, a sterilizing agent, filtration, irradiation, or heat.

Alternatively, the pharmaceutical compositions of the present disclosure are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the present disclosure will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition can be in the form of a capsule or cartridge (made, for example, from gelatin) comprising a compound of the present disclosure and a powder suitable for use in a powder inhaler. Suitable powder bases include, by way of example, lactose or starch.

The compounds of the present disclosure can also be administered transdermally using known transdermal delivery systems and excipients. For example, the active agent can be admixed with permeation enhancers, such as propylene glycol, polyethylene glycol monolaurate, azycycloalkan-2-ones and the like, and incorporated into a patch or similar delivery system. Additional excipients including gelling agents, emulsifiers and buffers, can be used in such transdermal compositions if desired.

If desired, the compounds of this present disclosure can be administered in combination with one or more other therapeutic agents. In this embodiment, a compound of this present disclosure is either physically mixed with the other therapeutic agent to form a composition containing both agents; or each agent is present in separate and distinct compositions which are administered to the patient simultaneously or sequentially.

For example, a compound of the present disclosure can be combined with a second therapeutic agent using conventional procedures and equipment to form a composition comprising a compound of the present disclosure (e.g., compounds A, B, C, and D and E, F, G, and H) and a second therapeutic agent. Additionally, the therapeutic agents can be combined with a pharmaceutically acceptable carrier to form a pharmaceutical composition comprising a compound of the present disclosure, a second therapeutic agent and a pharmaceutically acceptable carrier. In this embodiment, the components of the composition are typically mixed or blended to create a physical mixture. The physical mixture is then administered in a therapeutically effective amount using any of the routes described herein. Alternatively, the therapeutic agents may remain separate and distinct before administration to the patient. In this embodiment, the agents are not physically mixed together before administration but are administered simultaneously or at separate times as separate compositions. Such compositions can be packaged separately or can be packaged together as a kit. The two therapeutic agents in the kit can be administered by the same route of administration or by different routes of administration. Any therapeutic agent compatible with the compounds of the present disclosure can be used as the second therapeutic agent.

In an embodiment, multiple doses of the agent (e.g., compounds A, B, C, and D and E, F, G, and H, and/or prodrugs thereof) are contacted (e.g., administered). The frequency of administration of the agent can vary depending on any of a variety of factors, e.g., severity of the symptoms, and the like. For example, in an embodiment, the agent is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in an embodiment, the agent is administered continuously.

The duration of contacted (e.g., administered) of the agent, e.g., the period of time over which the agent is administered, can vary, depending on any of a variety of factors, e.g., patient response, etc. For example, the agent can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art.

In an embodiment of the present disclosure, an effective dosage may be in the range of 0.001-100 mg/kg/day, preferably 0.005-5 mg/kg/day. For an average 70 kg human, this would amount to 0.007-7000 mg per day, or preferably 0.05-350 mg/day. Alternatively, the administration of compounds as described by L. C. Fritz et al. in U.S. Pat. No. 6,200,969 is followed. One of skill in the art with this disclosure can create an effective pharmaceutical formulation.

Methods of Use

Embodiments of the present compounds (e.g., compounds noted in FIG. 1.1 and the related discussion and elsewhere in the application such as compounds A, B, C, D, 2'substituted nicotine compounds, azetidine compounds, and ether linked nicotine compounds (FIG. 1.2, compounds E, F, G, and H)) have been shown to be effective in treating conditions (CNS disorders (e.g., schizophrenia, Alzheimer's disease, Parkinson's disease, attention-deficit-hyperactivity disorder), treating drug addictions (e.g., smoking and alcoholism) and controlling inflammatory conditions (e.g., sepsis, acute pancreatitis, rheumatoid arthritis)). In addition, embodiments of the compounds can be used to selectively stimulate alpha7 nAChRs or alpha7 nAChRs and alpha4beta2 nAChRs. Additional details are provided in the Examples.

In general, the treatment methods typically comprise administering to a subject (e.g., human) having the condition a therapeutically effective amount of a compound of the present disclosure in one or more doses, alone or in combination with other agents (e.g., drugs or biologicals). For example, one or more compounds of the present disclosure is provided or administered to a subject having a CNS condition. In an embodiment, one or more compounds of the present disclosure can be used in combination with drugs or biologicals.

The present disclosure also provides methods of prophylactically treating a condition by administering an effective amount of a compound of the present disclosure in one or more doses, alone or in combination with other agents (e.g., drugs or biologicals) to a subject in need thereof.

As mentioned above, compounds of the present disclosure and pharmaceutical compositions can be used in combination of one or more other therapeutic agents for treating conditions. For example, compounds of the present disclosure and pharmaceutical compositions provided herein can be employed in combination with other agents.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Brief Introduction

The chemical and pharmacological properties of 2'-substituted nicotines are poorly understood relative to other substituted nicotines. Here, we report the synthesis of several racemic 2'-substituted nicotine analogs. As shown in FIG. 2.1, the N-oxide of nicotine was reacted successively with trifluoroacetic anhydride and potassium cyanide, generating (±)-2'-cyanonicotine 3 (58%). This was reacted with methylmagnesium bromide, ethylmagnesium bromide or n-propylmagnesium chloride, giving (±)-2'-methylnicotine 5 (95%), (±)-2'-ethylnicotine 6 (92%) and (±)-2'-n-propylnicotine 7 (94%). Reduction of 2'-cyanonicotine 3 with Dibal-H gave (±)-2'-aminomethylnicotine 8 (59%). This was treated successively with sodium nitrite in aqueous acetic acid and with potassium hydroxide in methanol, giving (±)-2'-hydroxymethylnicotine 9 (35%). The hydrolysis of 2'-cyanonicotine in a mixture of trifluoroacetic acid and sulphuric acid gave (±)-2'-carbamoylnicotine 10 (51%).

Introduction

Deficits in brain nicotinic acetylcholine receptor (nAChR) expression have been reported in neurodegenerative and mental diseases.[1,2] Therefore, nicotinic acetylcholine agonists are being developed to alleviate these deficits.[3,4] Nicotine addiction is also being treated with nAChR agonists, including nicotine.[5,6] While a variety of nicotine analogs have been synthesized and investigated using radioligand binding measurements, a comparative analysis of their functional effects on brain nAChRs has not yet been made. Synthetic methods for preparing 1',3'-, 4'- and 5'-substituted nicotine analogs have been reported. 2'-Methyl- and 2'-ethyl-nicotine were reported to displace the binding of radiolabeled methylcarbamylcholine to rat brain nAChRs that bind nicotine with high affinity.[7] However, their method of synthesis was not described.

The following procedures have been described for the synthesis of the 3'-, 4'- and 5'-substituted nicotine derivatives. In Scheme 1 (Example 1), FIG. 2.2, the reduction of (S)-cotinine with $NaAlH_4$ or with Red-Al gave the $\Delta^{1'(5')}$-iminium; this treated with KCN gave a mixture of 5'-cyanonicotine diastereomers.[8] Oxidation of (S)-nicotine 1 with mercuric acetate gave the iminium acetate, which was treated with KCN to generate (±)-2'-cyanonicotine (1%) in mixture with the 5'-cyanonicotine diastereomers (18%).[8,9] Hydrolysis of the mixture of 5'-cyanonicotine diastereomers with NaOH and $H_2O_2$ gave the 5'-carbamoylnicotine diastereomers.[9] The reaction of (S)-cotinine with (+)-(10-camphorsulfonyl)oxaziridine gave (3'R,5'S)-3'-hydroxycotinine.[10] Mesylation followed by the reduction of the keto group with $BH_3$ and the substitution of the mesylate with NaCN provided (2'S,4'S)-4'-cyanonicotine.[10] In an embodiment, one or more of the hydrogens on each of the rings can be substituted with an R (e.g., RP1 to RP6, RN1, and R2', R4', and R5') group as described herein and consistent with the reaction sequence described in Scheme 1, FIG. 2.2.

The reaction of LDA with (S)-cotinine gave its enolate; this was treated with formaldehyde to give the 3'-hydroxymethylcotinine diastereomers, which reacted with $BH_3$ to give a mixture of 4'-hydroxymethylnicotine diastereomers.[10] The reaction of the enolate of (S)-cotinine with methyliodide gave (3'RS,5'S)-3'-methylcotinine which, after treatment with $BH_3$ and separation of the major isomer, gave (2'S, 4'R)-4'-methylnicotine.[10] The reaction of (S)-cotinine with methyllithium gave an amino alcohol which was further treated with $NaBH_3CN$ to generate the mixture of 5'-methylnicotine diastereomers.[10]

The reaction of the imine N-3-pyridylidenemethylamine with succinic anhydride gave (±)-trans-4'-carboxycotinine;[11] reaction of its methyl ester with LAH gave (±)-trans-3'-hydroxymethylnicotine and its tosylate was reduced with LAH to give (±)-trans-3'-methylnicotine.

The (±)-trans-3'-, 4'- or 5'-carboxynicotines and the (±)-trans-4'-carboxycotinine reacted with an amidating reagent comprising ammonium bicarbonate and di-t-butyl dicarbonate to generate the corresponding amides.[12,13] Reduction of the amides with a hydride gave the (±)-trans-3'-, 4'- or 5'-aminomethylnicotines. These were also obtained from the (±)-trans-3'-, 4'- or 5'-hydroxymethylnicotines by reaction of their tosylates with ammonia.[14,15]

In the present Example, we report new synthetic methods for obtaining the following 2'-nicotine derivatives: (±)-2'-cyanonicotine 3, (±)-2'-methylnicotine 5, (±)-2'-ethylnicotine 6, (±)-2'-n-propylnicotine 7, (±)-2'-aminomethylnicotine 8, (±)-2'-hydroxymethylnicotine 9 and (±)-2'-carbamoylnicotine 10. The pharmacological properties of these racemic nicotines and their enantiomers, separated by chiral HPLC.

Results and Discussion

Initially, we examined the preparation of (±)-2'-methylnicotine by reacting 2-methyl-1-pyrroline with 3-pyridylmagnesium bromide (Scheme 2 (FIG. 2.3)). In an embodiment, one or more of the hydrogens on each of the rings can be substituted with an R (e.g., RP1 to RP6, RN1, and R2', R4', and R5') group as described herein and consistent with the reaction sequence described in Scheme 2, Example 1, FIG. 2.3.

Reaction of an organometallic reagent with a cyclic imine group has been described in the literature. Methyllithium has been added to a 1-alkyl-3,4-dihydroisoquinoline to generate 1-alkyl-1-methyl-1,2,3,4-tetrahydroisoquinoline.[16] Allylmagnesium bromide has been reacted with 2-methyl-1-pyrroline, giving a 2-allyl-2-methyl-pyrrolidine.[17]

In this Example, 3-pyridylmagnesium bromide,[18] 3-pyridylmagnesium chloride[19] and 3-pyridyllithium[18] were prepared from 3-bromopyridine. The addition of each of these organometallics to 2-methyl-1-pyrroline was attempted at −50° C. or −78° C. In the case of the addition of pyridylmagnesium bromide or chloride, boron trifluoride-diethyl etherate was added prior to the addition of the Grignard reagent. However, 2'-methyl-2'-(pyridyl-3)-pyrrolidine was not obtained.

The imine bond can be activated by quaternization to allow the nucleophilic addition of Grignard reagent. Methyl iodide was added to 1-methyl-3,4-dihydroisoquinoline, generating the iminium salt 1,2-dimethyl-3,4-dihydroisoquinolinium iodide.[20] This iminium salt is more reactive than the imine. Methylmagnesium chloride reacted with the iminium, generating 1,1,2-trimethyl-1,2,3,4-tetrahydroisoquinoline. The reaction of methylmagnesium chloride with the iminium salt N-isopropylidene-4-chloropiperidinium chloride gave 1-tert-butyl-4-chloropiperidine.[21]

Expecting a higher reactivity for the iminium salt than for the imine, in this research 2-methyl-1-pyrroline was transformed with methyl iodide into the iminium 1,2-dimethyl-1-pyrrolinium iodide (Scheme 2 (FIG. 2.3)). The condensation of this iminium with 2 or 5 equivalents of 3-pyridylmagnesium bromide or chloride was attempted in THF or in the mixture of THF with diethyl ether, first at 0° C., then at room temperature and in some cases ending with heating to reflux. However, 2'-methylnicotine was never obtained.

In another approach, the iminium 1,2-dimethyl-1-pyrrolinium iodide in dichloromethane was reacted with an aqueous solution of potassium cyanide at rt (Scheme 2 (FIG. 2.3)). The 1,2-dimethyl-2-cyanopyrrolidine was obtained in 95% yield. Its condensation with 5 equivalents of 3-pyridylmagnesium bromide was attempted in THF at 0° C., followed by rt and in some cases by heating to reflux. However the Bruylants reaction did not take place and 2'-methylnicotine was never obtained.[22-24] It only resulted in recovered starting material.

The probable reason that the condensations of 3-pyridylmagnesium chloride or bromide with 2-methyl-1-pyrroline, 1,2-dimethyl-1-pyrrolinium iodide or 1,2-dimethyl-2-cyano-pyrrolidine did not succeed is steric hindrance due both to the reagents and to the desired product, 2'-methylnicotine. Also, the deprotonation of the methyl group of the 2-methyl-1-pyrroline and the iminium salt was probably competing with the desired addition, which would explain the recovery of the starting imine or iminium.

To circumvent these problems, we developed a practical synthesis of the key intermediate (±)-2'-cyanonicotine 3 using the Polonovski reaction.[25,26] The N-oxides 2 of nicotine were reacted with trifluoroacetic anhydride; the iminium intermediate then reacted with the cyano ion (Scheme 3 FIG. 2.4). In practice, (S)-Nicotine 1 was transformed by m-CPBA into the diastereomeric mixture of N-oxides 2 with a yield of 97%. Trifluoroacetic anhydride transformed in dichloromethane at 0° C. the N-oxides 2 into the $\Delta^{1',2'}$ iminium trifluoroacetate. Thereafter, addition of solid potassium cyanide to the reaction mixture yielded (±)-2'-cyanonicotine 3 (58% from 2). A small amount of the of 5'-cyanonicotine diastereomers 4 (12%) was also formed; these diastereomers were separated by silica gel column chromatography into the trans and cis isomers.

The cyano group in amino nitrile 3 is in a position to the tertiary amine. The substitution of this cyano group by an organomagnesium compound was made according to the Bruylants reaction.[22-24] The displacement of the cyano group led to an intermediate stabilized iminium carbocation which reacted further with the nucleophile alkyl organomagnesium. The reaction of 5 equivalents of methyl-, ethylmagnesium bromide or n-propylmagnesium chloride with amino nitrile 3 in THF at −10° C. generated the (±)-2'-methyl- (5), (f)-2'-ethyl- (6), and (±)-2'-n-propylnicotine (7) with respective yields of 95, 92 and 94%.

The transformation of the cyano group of the amino nitrile 3 gave several (±)-2'-derivatives of nicotine. DIBALH in toluene at −78° C. reduced the amino nitrile 3 into (±)-2'-aminomethylnicotine 8 in 59% yield.

The (±)-2'-aminomethylnicotine 8 was first treated with sodium nitrite in aqueous acetic acid; the reaction mixture was made alkaline and extracted with dichloromethane. After rotary evaporation the resulting organic extract was treated with potassium hydroxide in methanol, giving (±)-2'-hydroxymethylnicotine 9 in 35% yield.

The hydrolysis of the (±)-2'-cyanonicotine 3 in a mixture of trifluoroacetic acid and sulphuric acid (4:1) gave (±)-2'-carbamoylnicotine 10 in 51% yield.

In an embodiment, one or more of the hydrogens on each of the rings can be substituted with an R (e.g., RP1 to RP6, RN1, and R2', R4', and R5') group as described herein and consistent with the reaction sequence described in Scheme 2, Example 1, FIGS. 2.4 and 2.5.

FIG. 2.6 illustrates effects of methylation on binding are consistent with the alpha4beta2 (Top) and alpha7 (bottom) nAChRs determined with radiolabeled cytisine effects on functional potency EC50 measured with oocytes. Ki s for binding to rat and alpha-bungarotoxin, respectively (The numbers for (S)-nicotine are shown within the ring).

FIG. 2.6 illustrates effects of methylation on binding are consistent with the effects on functional potency EC50 measured with oocytes.

FIG. 2.7 illustrates the initial reactions for synthesis of 2'-substituted nicotines.

FIG. 2.8 illustrates the alkylation of an imine intermediate of the 2'-cyanonicotine at the 2' position with appropriate Grignard reagents.

FIG. 2.9 illustrates the preparation of 2' aminoalkyl and carboxamido-nicotines from 2'-cyanonicotine.

FIG. 2.10 illustrates a comparison of 2'Methyl-nicotine (■) with nicotine (●) in oocytes expressing α7 receptors. The methylated nicotine displays a 6.7-fold increase in potency at this nAChR relative to nicotine.

FIG. 2.11 illustrates a comparison of 5' Trans-Me-Nic (■) with 5' Cis-Me-Nic (◆) in oocytes expressing α7 receptors. The trans enantiomer activity is similar to nicotine on this receptor.

FIG. 2.12 illustrates a comparison of 5' Trans-Me-Nicotine (■) with 5' Cis-Me-Nicotine (◆) in oocytes expressing α4β2 receptors Both the cis- and trans-enantiomers are inactive on α4β2 receptors.

FIG. 2.13 illustrates a comparison of 5' Trans-Me-Nic (■) with 5' Cis-Me-Nic (◆) in oocytes expressing α6/α3 chimera/β2 receptors. The alpha6beta2 receptor responds in an essentially identical manner to the two 5'-methyl nicotine enantiomers.

It should be noted for the synthesis steps described, the components (e.g., methyl iodide can be alkyl halogenide) in the reactions can be changed consistent with teachings described herein.

Experimental Section

General: ESI–HRMS were performed on a Agilent 6210 TOF mass spectrometer. GC/CI analyses were performed on a Thermo Trace GC DSQ-Single Quadrupole. The $^1$H NMR spectra were recorded in CDCl$_3$ at 300 MHz with a Varian Mercury 300 and are reported in ppm from internal TMS on the δ scale. The $^{13}$C NMR spectra were recorded in CDCl$_3$ at 75.4 MHz with a Varian Mercury 300 instrument. Chromatographies were performed on silica gel columns (Fisher, Silica Gel Sorbent, 230-400 Mesh) using the flash technique or on alumina (Aluminoxid 90, Activity EMD).

Nicotine-N-oxides (2). To a solution of (S)-nicotine (4 mL, 25.04 mmol) in CH$_2$Cl$_2$ (120 mL) at 0° C. was added a 70% aq m-CPBA (6.172 g, 25.04 mmol). After stirring 1 h 30 at 0° C. under argon, the reaction mixture was concentrated in vacuo to a volume of 10 mL and then poured over alumina and chromatographed using CH$_2$Cl$_2$/CH$_3$OH (98:2 to 95:5) as eluent to afford a diasteromeric mixture of trans- and cis-nicotine-N-oxide 2 (4.354 g, 24.4 mmol, 97%).

(±)-2'-Cyanonicotine (3). Trifluoroacetic anhydride (3.42 ml, 24.4 mmol) was slowly added under argon atmosphere to a solution of N-oxides 2 (2.177 g, 12.2 mmol) in dry methylene chloride (30 ml) cooled to 0° C. The resulting mixture was stirred at 0° C. for 1 h and at room temperature for 15 min. Following this period excess solid potassium cyanide (1.586 g, 24.4 mmol) was added to the reaction mixture and vigorous stirring was continued for 3 h. The reaction mixture was then basified with saturated aqueous sodium carbonate and extracted with methylene chloride (3×40 mL). The combined organic layers were dried over anhydrous magnesium sulfate and concentrated. After column chromatography of the crude product on silica gel (CH$_2$Cl$_2$/CH$_3$OH/NH$_4$OH coned 95:5:0.1), pure (±)-2'-cyanonicotine 3 was obtained as a colorless oil (1.325 g, 7.08 mmol, 58%) as well as cis- and trans-5'-cyanonicotine 4 (0.274 g, 1.46 mmol, 12%) as a colorless oil. $^1$H NMR (300 MHz, CDCl$_3$) 3: δ=8.86 (d, 1H, J=2.4 Hz, ArH), 8.61 (dd, 1H, J=1.8, 4.8 Hz, ArH), 7.90 (dt, 1H, J=8.1, 2.4 Hz, ArH), 7.34 (ddd, 1H, J=8.1, 5.1, 0.9 Hz, ArH), 3.37 (m, 1H), 2.71 (m, 1H), 2.57 (m, 1H), 2.25 (s, 3H, NCH$_3$), 2.16-2.02 (m, 3H). —$^{13}$C NMR (75.3 MHz, CDCl$_3$): δ=150.0 (CH), 148.0 (CH), 134.1 (CH), 133.9 (C), 123.5 (CH), 116.8 (CN), 69.7 (C), 53.8 (CH$_2$), 43.1 (CH$_2$), 36.2 (CH$_3$), 21.1 (CH$_2$). HRMS (ESI) m/z: found for [M+H]$^+$ 188.1175, Calcd for C$_{11}$H$_{14}$N$_3$ 188.1182.

Subsequently, the mixture of cis- and trans-5'-cyanonicotine 4 was separated by HPLC with a Beckman Coulter Ultrasphere silica column (10×250 mm), using a 2% B to 20% B 25 min gradient (solvent A: Hexane-DEA [99.5, 0.5 v/v]; solvent B: EtOH-DEA [99.5, 0.5]), preceded by 10 min elution at 2% B. The flow rate was 2.7 mL/min and column temperature was 24° C. The eluate was monitored at 260 nm. In this way, trans-5'-cyanonicotine (4a, 182 mg, 8%) eluting at 17.8 min and cis-5'-cyanonicotine (4b, 91 mg, 4%) eluting at 25.7 min, were isolated.

trans-5'-Cyanonicotine (4a). $^1$H NMR (300 MHz, CDCl$_3$): δ=8.57 (d, 1H, J=2.1 Hz, ArH), 8.54 (dd, 1H, J=1.8, 4.8 Hz, ArH), 7.65 (dt, 1H, J=8.1, 1.8 Hz, ArH), 7.29 (ddd, 1H, J=8.1, 5.1, 0.9 Hz, ArH), 4.16 (d, 1H, J=8.1 Hz), 3.59 (t, 1H, J=7.2 Hz), 2.45 (m, 2H), 2.30 (s, 3H, NCH$_3$), 2.19 (m, 1H), 1.80 (m, 1H). —$^{13}$C NMR (75.3 MHz, CDCl$_3$): δ=149.6 (CH), 149.5 (CH), 135.0 (CH), 134.1 (C), 123.9 (CH), 117.5 (CN), 65.4 (CH), 56.9 (CH), 36.8 (CH$_3$), 33.4 (CH$_2$), 28.7 (CH$_2$). HRMS (ESI) m/z: found for [M+H]$^+$ 188.1176. Calcd for C$_{11}$H$_{14}$N$_3$ 188.1182.

cis-5'-Cyanonicotine (4b). $^1$H NMR (300 MHz, CDCl$_3$): δ=8.55 (dd, 1H, J=1.8, 4.8 Hz, ArH), 8.53 (d, 1H, J=2.1 Hz, ArH), 7.74 (dt, 1H, J=7.8, 2.1 Hz, ArH), 7.30 (ddd, 1H, J=8.1, 5.1, 0.9 Hz, ArH), 3.39 (t, 2H, J=7.1 Hz), 2.33 (s, 3H, NCH$_3$), 2.29 (m, 3H), 1.88 (m, 1H). —$^{13}$C NMR (75.3 MHz, CDCl$_3$): δ=149.6 (CH), 149.5 (CH), 138.5 (C), 134.9 (CH), 124.1 (CH), 117.0 (CN), 68.1 (CH), 55.9 (CH), 39.0 (CH$_3$), 34.2 (CH$_2$), 28.7 (CH$_2$). HRMS (ESI) m/z: found for [M+H]$^+$ 188.1176. Calcd for C$_{11}$H$_{14}$N$_3$ 188.1182.

(±)-2'-Methylnicotine (5). A solution of methylmagnesium bromide (3 M solution in ether, 445 μL, 1.335 mmol) was added dropwise to a solution of 2'-cyanonicotine 3 (50 mg, 0.27 mmol) in THF (2 mL) cooled to −10° C. The mixture was stirred at −10° C. for 1 h followed by 1 h at room temperature and then hydrolysed by a saturated aqueous solution of NH$_4$Cl (5 mL). The mixture was extracted with methylene chloride. The organic extracts were dried and evaporated to give an oil which was purified by flash chromatography on silica gel (CH$_2$Cl$_2$/CH$_3$OH/NH$_4$OH concd 95:5:0.1) to give (±)-2'-methylnicotine 5 as a clear oil (45.2 mg, 0.26 mmol, 95%). $^1$H NMR (300 MHz, CDCl$_3$): δ=8.71 (d, 1H, J=1.5 Hz, ArH), 8.45 (dd, 1H, J=1.8, 4.8 Hz, ArH), 7.81 (dt, 1H, J=8.1, 1.8 Hz, ArH), 7.23 (ddd, 1H, J=8.1, 5.1, 0.6 Hz, ArH), 3.11 (m, 1H), 2.70 (m, 1H), 2.12 (s, 3H, NCH$_3$), 1.90 (m, 4H) 1.34 (s, 3H, CH$_3$). —$^{13}$C NMR (75.3 MHz, CDCl$_3$): δ=148.6 (CH), 147.7 (CH), 143.0 (C), 134.2 (CH), 123.1 (CH), 64.1 (C), 53.4 (CH$_2$), 43.3 (CH$_2$), 34.9 (CH$_3$), 22.0 (CH$_2$), 16.9 (CH$_3$). HRMS (ESI) m/z: found for [M+H]$^+$ 177.1381, Calcd for C$_{11}$H$_{17}$N$_2$ 177.1386. found for [2M+H]$^+$=353.2686. Calcd for C$_{22}$H$_{33}$N$_4$ 353.2700.

(±)-2'-Ethylnicotine (6). A solution of ethylmagnesium bromide (1 M solution in THF, 1.23 mL, 1.23 mmol) was added dropwise to a solution of 2'-cyanonicotine 3 (46 mg, 0.25 mmol) in THF (1 mL) cooled to −10° C. The mixture was stirred at −10° C. for 1 h then at room temperature for 16 h. After addition of a saturated aqueous solution of NH$_4$Cl (3 mL), the mixture was extracted with methylene chloride. The organic extracts were dried and evaporated to give an oil which was purified by flash chromatography on silica gel (CH$_2$Cl$_2$/CH$_3$OH/NH$_4$OH concd 95:5:0.1) to give (±)-2'-ethylnicotine 6 as a clear oil (44 mg, 0.23 mmol, 92%). $^1$H NMR (300 MHz, CDCl$_3$): δ=8.55 (d, 1H, J=2.7 Hz, ArH), 8.47 (dd, 1H, J=1.8, 4.8 Hz, ArH), 7.59 (dt, 1H, J=8.1, 2.1 Hz, ArH), 7.27 (ddd, 1H, J=7.8, 5.1, 0.6 Hz, ArH), 2.92 (m, 1H), 2.48 (m, 1H), 2.27 (m, 2H), 2.10 (s, 3H, NCH$_3$), 1.93 (m, 4H), 1.60 (m, 1H), 0.83 (t, 3H, J=7.2 Hz). —$^{13}$C NMR (75.3 MHz, CDCl$_3$): δ=149.3 (CH), 147.8 (CH), 136.6 (C), 135.3 (CH), 122.9 (CH), 67.6 (C), 53.9 (CH$_2$), 36.7 (CH$_2$), 35.1 (CH$_3$), 29.1 (CH$_2$), 22.0 (CH$_2$), 10.0 (CH$_3$). HRMS (ESI) m/z: found for [M+H]$^+$ 191.1548, Calcd for C$_{12}$H$_{19}$N$_2$ 191.1543. found for [2M+H]$^+$=381.3008. Calcd for C$_{24}$H$_{37}$N$_4$ 381.3013.

(±)-2'-n-Propylnicotine (7). A solution of n-propylmagnesium chloride (2 M solution in ether, 334 μL, 0.67 mmol) was added dropwise to a solution of 2'-cyanonicotine 3 (25 mg, 0.13 mmol) in THF (1 mL) cooled to −10° C. The mixture was stirred at −10° C. for 1 h then at room temperature for 16 h. After addition of a saturated aqueous solution of NH$_4$Cl (3 mL), the mixture was extracted with methylene chloride. The organic extracts were dried and evaporated to give an oil which was purified by flash chromatography on silica gel (CH$_2$Cl$_2$/CH$_3$OH/NH$_4$OH concd 95:5:0.1) to give (±)-2'-n-propylnicotine 7 as a clear oil (25 mg, 0.12 mmol, 94%). $^1$H NMR (300 MHz, CDCl$_3$): δ=8.54 (d, 1H, J=2.1 Hz, ArH), 8.46 (dd, 1H, J=1.5, 4.8 Hz, ArH), 7.57 (dt, 1H, J=8.1, 1.8 Hz, ArH), 7.26 (ddd, 1H, J=8.1, 4.8, 0.6 Hz, ArH), 2.89 (m, 1H), 2.47 (m, 1H), 2.21 (m, 2H), 2.10 (s, 3H, NCH$_3$), 1.99 (m, 3H), 1.52 (td, 1H, J=5.1, 12.0 Hz), 1.20 (m, 2H), 0.93 (t, 3H, J=7.2 Hz). —$^{13}$C NMR (75.3 MHz, CDCl$_3$): δ=149.3 (CH), 147.8 (CH), 137.0 (C), 135.2 (CH), 122.9 (CH), 67.1 (C), 53.7 (CH$_2$), 39.1 (CH$_2$), 37.3 (CH$_2$), 35.2 (CH$_3$), 22.2 (CH$_2$), 19.0 (CH$_2$), 15.1 (CH$_3$). HRMS (ESI) m/z: found for [M+H]$^+$ 205.1695, Calcd for C$_{13}$H$_{21}$N$_2$205.1699.

(±)-2'-Aminomethylnicotine (8). A solution of 2'-cyanonicotine 3 (324 mg, 1.73 mmol) in toluene (12.4 mL) was treated at −78° C. with DIBALH (8.65 mL of a 1.0 M solution in hexane, 8.65 mmol). After the reaction mixture had been stirred for an additional 3 h at −78° C., it was quenched by slow addition of saturated aqueous solution of NH$_4$Cl. The resulting mixture was allowed to warm to room temperature. The organic layer was separated and the aqueous layer was extracted with methylene chloride. The combined organic extracts were dried over MgSO$_4$ and concentrated in vacuo. The crude mixture was purified by flash chromatography on silica gel (CH$_2$Cl$_2$/CH$_3$OH/NH$_4$OH concd 95:5:0.1) to give (±)-2'-aminomethylnicotine 8 as a clear oil (195.1 mg, 1.02 mmol, 59%) as well as nicotine (11 mg, 0.07 mmol, 4%). $^1$H NMR (300 MHz, CDCl$_3$): δ=8.60 (d, 1H, J=2.7 Hz, ArH), 8.48 (dd, 1H, J=1.8, 4.8 Hz, ArH), 7.64 (dt, 1H, J=8.1, 1.8 Hz, ArH), 7.28 (ddd, 1H, J=8.1, 4.8, 0.9 Hz, ArH), 3.21 (d, 1H, J=12.9 Hz), 3.03 (d, 1H, J=12.9 Hz), 3.00 (m, 1H), 2.74 (m, 1H), 2.18 (m, 2H), 2.17 (s, 3H, NCH$_3$), 1.93 (m, 2H), 1.32 (bs, 2H, NH$_2$). —$^{13}$C NMR (75.3 MHz, CDCl$_3$): δ=149.1 (CH), 148.0 (CH), 138.3 (C), 135.0 (CH), 123.2 (CH), 68.0 (C), 54.8 (CH$_2$), 46.5 (CH$_2$), 36.5 (CH$_2$), 35.5 (CH$_3$), 22.5 (CH$_2$). HRMS (ESI) m/z: found for [M+H]$^+$ 192.1490. Calcd for C$_{11}$H$_{17}$N$_3$ 192.1495.

(±)-2'-Hydroxymethylnicotine (9). A solution of 8 (51 mg, 0.27 mmol) in 50% aqueous acetic acid (2 mL) was treated with NaNO$_2$ (37 mg, 0.54 mmol), and the resulting mixture was stirred at room temperature for 24 h. The reaction mixture was then basified with 40% aqueous NaOH and extracted with methylene chloride. The organic extract was treated with a solution of 5% KOH/MeOH (5 mL) for 4 h. The reaction mixture was washed with water and the organic layer was concentrated in vacuo. Chromatographic purification (SiO$_2$, elution with CH$_2$Cl$_2$/CH$_3$OH/NH$_4$OH concd 95:5:0.1) of the residue afforded (±)-2'-hydroxymethylnicotine 9 (18 mg, 0.095 mmol, 35%) as a colorless oil. $^1$H NMR (300 MHz, CDCl$_3$): δ=8.55 (d, 1H, J=2.4 Hz, ArH), 8.49 (dd, 1H, J=1.5, 4.5 Hz, ArH), 7.59 (dt, 1H, J=8.4, 1.8 Hz, ArH), 7.28 (ddd, 1H, J=8.1, 4.8, 0.9 Hz, ArH), 3.97 (d, 1H, J=10.5 Hz), 3.79 (d, 1H, J=10.5 Hz), 3.16 (m, 1H), 2.88 (m, 1H), 2.39 (m, 1H), 2.14 (s, 3H, NCH$_3$), 1.95 (m, 3H). —$^{13}$C NMR (75.3 MHz, CDCl$_3$): δ=148.7 (CH), 148.3 (CH), 138.4 (C), 134.7 (CH), 123.3 (CH), 67.6 (C), 63.0 (CH$_2$), 55.3 (CH$_2$), 36.7 (CH$_2$), 35.2 (CH$_3$), 22.7 (CH$_2$). HRMS (ESI) m/z: found for [M+H]$^+$ 193.1330, Calcd for C$_{11}$H$_{17}$N$_2$O, 193.1335. found for [2M+H]$^+$=385.2585, Calcd for C$_{22}$H$_{33}$N$_4$O$_2$ 385.2598.

(±)-2'-Carbamoylnicotine (10). A solution of 2'-cyanonicotine 3 (89 mg, 0.48 mmol) in 4 mL of a solution TFA/concd H$_2$SO$_4$ (4:1) was stirred at 50° C. for 20 h. After cooled at 0° C., the mixture was basified by addition of NH$_4$OH concd and extracted with methylene chloride. The combined organic extracts were dried over MgSO$_4$ and concentrated in vacuo. The crude mixture was purified by flash chromatography on silica gel (CH$_2$Cl$_2$/CH$_3$OH/NH$_4$OH concd 95:5:0.1) to give (±)-2'-carbamoylnicotine 10 as a yellow solid (50 mg, 0.24 mmol, 51%). $^1$H NMR (300 MHz, CDCl$_3$): δ=8.54 (d, 1H, J=2.1 Hz, ArH), 8.51 (dd, 1H, J=1.2, 4.8 Hz, ArH), 7.59 (dt, 1H, J=7.8, 2.1 Hz, ArH), 7.48 (bs, 1H), 7.29 (ddd, 1H, J=8.1, 4.8, 0.9 Hz, ArH), 6.58 (bs, 1H), 3.11 (m, 1H), 2.56 (m, 3H), 2.03 (m, 2H), 1.99 (s, 3H, NCH$_3$). —$^{13}$C NMR (75.3 MHz, CDCl$_3$): δ=177.8 (C), 149.8 (CH), 148.6 (CH), 136.4 (CH), 133.7 (C), 122.8 (CH), 73.7 (C), 54.9 (CH$_2$), 38.7 (CH$_2$), 37.4 (CH$_3$), 23.0 (CH$_2$). HRMS (ESI) m/z: found for [M+H]$^+$206.1283, Calcd for C$_{11}$H$_{16}$N$_3$O, 206.1288. found for [2M+H]$^+$=411.2495. Calcd for C$_{22}$H$_{31}$N$_6$O$_2$ 411.2503.

REFERENCES FOR EXAMPLE 1, EACH OF WHICH ARE INCORPORATED HEREIN BY REFERENCE

1. Newhouse, P. A.; Sunderland, Y.; Tariot, P. N.; Blumhardt, C. L.; Weingartner, H.; Mellow, A. *Psychopharmacology*, 1988, 95, 171-175.
2. Freedman, R.; Hall, M.; Adler, L. E.; Leonard, S. *Biol Psychiatry*, 1995, 38, 22-33.
3. Freedman, R.; Olincy, A.; Buchanan, R. W.; Harris, J. G.; Gold, J. M.; Johnson, L.: Allensworth, D.; Guzman-Bonilla, A. G.; Bettye, B. A.; Clement, M. S. W.; Ball, M. P.; Kutnick, C. J.; Pender, V.; Laura F. Martin, L. F.; Stevens, K. M.; Wagner, B. D.; Zerbe, G. O.; Soti, F.; Kem, W. R. *Amer. J. Psychiat.*, 2008, 165, 1040-1047.
4. Taly, A.; Corringer, P.-J.; Guedin, D.; Lestage, P.; and Changeux, J.-P. *Nature Revs Drug Discov.*, 2009, 733-750.
5. Benowitz, N. L. *New Engl. J Med*, 2010, 362, 2295-303.
6. Rollema, H.; Coe, J. W.; Chambers, L. K.; Hurst, R. S.; Stahl, S. M.; Williams, K. E. *Trends Pharmacol. Sci.*, 2007, 28, 316-25.
7. Wang, D. X.; Booth, H.; Lerner-Marmarosh, N.; Osdene, T. S.; Abood, L. G. *Drug Development Res.*, 1998, 45, 10-16.
8. Peterson, L. A.; Trevor, A.; Castagnoli, N. Jr. *J. Med. Chem.*, 1987, 30, 249-254.
9. Hubert-Brierre, Y.; Herlem, D.; Khuong-Huu, F. *Tetrahedron*, 1975, 31, 3049-3054.
10. Lin, N. H.; Carrera, G. M. Jr.; Anderson, D. J. *J. Med. Chem.*, 1994, 37, 3542-3553.
11. Cushman, M.; Castagnoli, N. Jr. *J. Org. Chem.*, 1972, 37, 1268-1271.
12. Ennifar, S. PCT Int. Appl., 2007, WO 2007064478 A2 20070607.
13. Pozdnev, V. F. *Tetrahedron Lett.*, 1995, 36, 7115-7118.
14. Bachmann, M. F.; Maurer, P. PCT Int. Appl., 2004, WO 2004009116 A2 20040129.
15. Pierce, J. H.; Richards, H. C.; Shoppee, C. W.; Stephenson, R. J.; Summers, G. H. R. *J. Chem. Soc.*, 1955, 694-703.
16. Czamocki, Z.; Suh, D.; MacLean, D. B.; Hultin, P. G.; Szarek, W. A. *Can. J. Chem*, 1992, 70, 1555-1561.
17. Arai, T.; Abe, H.; Aoyagi, S.; Kibayashi, C. *Tetrahedron Lett.*, 2004, 45, 5921-5924.
18. Guthikonda, R. N.; Cama, L. D.; Quesada, M.; Woods, M. F.; Salzmann, T. N.; Christensen, B. G. *J. Med. Chem.*, 1987, 30, 871-880.
19. Trecourt, F.; Breton, G.; Bonnet, V.; Mongin, F.; Marsais, F.; Queguiner, G. *Tetrahedron Lett.*, 1999, 40, 4339-4342.
20. Heer, J. P.; Harling, J. D.; Thompson, M. *Synth. Commun.*, 2002, 32, 2555-2563.
21. Amato, J. S.; Chung, J. Y. L.; Cvetovich, R. J.; Gong, X.; McLaughlin, M.; Reamer, R. A. *J. Org. Chem.*, 2005, 70, 1930-1933.
22. Rouchaud, A.; Kem, W. R. *J. Het. Chem.*, 2010, 47, 569-581.
23. Frances, B.; Gouarderes, C.; Moisand, C.; Cros, J.; Jimonet, P.; Moy, L.; Chiaroni, A.; Riche, C.; Grierson, D. S.; Husson, H. P. *Eur. J. Med. Chem.*, 1992, 27, 369-381.
24. Rouchaud, A.; Braekman, J.-C. *Eur. J. Org. Chem.*, 2009, 2666-2674.

25. Grierson, D. S.; Harris, M.; Husson, H. P. *J. Am. Chem. Soc.*, 1980, 102, 1064-1082.
26. Grierson, D. S. *Org. React.*, 1990, 39, 85-295.

Example 2

Synthesis of Substituted Azetidinyl Analogs of Nicotine

As we found the four-membered saturated ring analog (trans-3-(1-methylazetidin-2-yl)pyridine) of nicotine to be a more potent strong agonist at both of the precognitive nicotinic acetylcholine receptors ($\alpha 7$ and $\alpha 4\beta 2$), we synthesized a racemic analog of this compound where an additional methyl substituent is present at the adjacent carbon (trans-3-(1,4-Dimethylazetidin-2-yl)pyridine). The additional methyl occurs at a position analogous to that of 5' methyl-nicotine. We reported earlier in this application that when this methyl is trans to the pyridyl substituent at position 2', that the compound is acceptable as an $\alpha 7$ agonist with nearly the same potency as the parent compound, but at $\alpha 4\beta 2$ receptors the trans form like the cis form has greatly reduced potency. Thus, the presence of a trans-methyl substituent creates considerable $\alpha 7$ selectivity of action. The synthesis of trans-3-(1,4-Dimethylazetidin-2-yl)pyridine and its azetidinone precursors is now described below.

FIG. 3.1 illustrates the first step in the synthesis of 4-azetidinone precursor of methylated azetidinyl analogs of nicotine. The precursor can be commercially obtained in chiral forms where the 3-position of the propionyl group is (S)- or (R) form, leading to (S)- or (R) forms of the nicotine analog.

FIG. 3.2 illustrates the preparation of the N-methyl-azetidinone precursor in the synthesis of 3-(1,4-dimethyl-azetidin-2-yl)pyridine.

FIG. 3.3 illustrates the final step in the synthesis of a 4'-methylated azetidinyl analog of nicotine incorporating a methyl substituent equivalent to the 5'-methyl in nicotine that can affect nAChR selectivity.

FIG. 3.4 is a graph that illustrates the effects of trans-3-(1,4-dimethylazetidin-2-yl)pyridine (■) and cis-3-(1,4-dimethylazetidin-2-yl)pyridine (♦) on $\alpha 4\beta 2$ receptors expressed in oocytes. The trans-diastereomers are significantly more potent than the cis-diastereomers, as in the 5'-methylnicotines.

FIG. 3.5 illustrates a methyl-azetidinone intermediate in the synthesis of the methyl azetidinyl analog of nicotine.

It should be noted for the synthesis steps described, the components (e.g., methyl iodide can be alkyl halogenide) in the reactions can be changed consistent with teachings described herein.

4-(Pyridin-3-yl)azetidin-2-one

To a mixture of 20.20 g (0.24 mole) sodium bicarbonate (Sigma, Ultrapure, dried in good vacuum at room temperature for 3 days over phosphorus pentoxide) and 6.64 g (0.04 mole) 3-amino-3-(pyridine-3-yl)propionic acid (Tyger, dried in good vacuum at room temperature for 3 days over phosphorus pentoxide) under argon atmosphere first 200 ml of dry acetonitrile (Fisher) was added then at very strong stirring 4.7 ml (0.044 mole) trifluormethanesulfonyl chloride (Acros) was slowly added and thereafter the reaction mixture was further stirred in an oil bath of 75-80° C. for 19 hours. After cooling and stirring in ice bath for 1 hour the reaction mixture was filtered, washed three times with dry acetonitrile and the combined organic solutions were evaporated on a rotavapor at 35° C. The solid residue (23.8 g) was extracted in a Soxhlet-type extractor with boiling chloroform for 26 hours. The evaporation of the chloroform solution gave 2.48 g (42%) pure product as white crystalline material (mp: 115-116° C.).

$^1$H-NMR: 8.62 (1H, d, J=2.4 Hz), 8.59 (1H, dd, J=4.8, 2.1 Hz), 7.74 (1H, dt, J=7.8, 1.8 Hz), 7.34 (1H, ddd, J=8.1, 4.8, 0.6 Hz), 6.45 (1H, br s), 4.78 (1H, dd, J=5.4, 2.4 Hz), 3.52 (1H, ddd, J=15.0, 5.4, 2.7 Hz), 2.92 (1H, ddd, J=15.0, 2.7, 0.9 Hz).

$^{13}$C-NMR: 167.68, 149.53, 147.62, 135.75, 133.10, 123.69, 48.04, 47.83.

1-Methyl-4-(pyridin-3-yl)azetidin-2-one

To a solution of 0.105 g (0.71 mmole) 4-(pyridin-3-yl)azetidin-2-one in 5 ml of dry tetrahydrofuran at stirring under argon atmosphere 0.113 g (2.83 mmole) 60% dispersion of sodium hydride in mineral oil was added. After the sparkling ceased at stirring and ice cooling 0.066 ml (0.150 g, 1.06 mmole) iodomethane was added and stirred for 2 hours. Carefully 10 ml of saturated aqueous ammonium chloride solution was added and stirred for 10 minutes. The reaction mixture was filtered and the aqueous solution was extracted with 5×10 ml of chloroform and the combined solutions were dried over magnesium sulfate and evaporated on rotavapor at 35° C. The residue (0.112 g) was purified by column chromatography on 10 g of silica gel with benzene-diethylamine 8-2 furnishing 0.0674 g (59%) pure product.

$^1$H-NMR: 8.62 (1H, dd, J=4.8, 1.8 Hz), 8.59 (1H, dd, J=2.7, 0.9 Hz), 7.65 (1H, dt, J=7.8, 1.8 Hz), 7.36 (1H, ddd, J=7.8, 4.8, 0.6 Hz), 4.54 (1H, dd, J=5.4, 2.4 Hz), 3.45 (1H, ddq, J=14.7, 5.4, 0.9 Hz), 2.87 (1H, ddq, J=14.7, 2, 4, 0.9 Hz), 2.78 (3H, t, J=0.9 Hz).

Cis- and trans-3-(1,4-Dimethylazetidin-2-yl)pyridine

All glassware was dried at 120° C. in an oven for overnight and the reaction was carried out under argon atmosphere.

To a solution of 0.0659 g (0.406 mmole) 1-methyl-4-(piridin-3-yl)azetidin-2-one in 2 ml dry tetrahydrofuran at ice cooling and stirring 0.38 ml (0.609 mmole) 1.6 M methyllithium solution in diethyl ether was added drop by drop from a syringe in 10 minutes and the reaction mixture was stirred for an additional 10 minutes at ice cooling and for 75 minutes at room temperature. To the reaction mixture 2 ml water was added, separated and the aqueous phase was extracted with 5×5 ml ether. The combined organic solutions were dried over magnesium sulfate and evaporated at 35° C. The residue (0.0403 g) was dissolved in 2 ml of dry methanol, cooled to −78° C. and at stirring 0.030 g (0.793 mmole) of sodium borohydride was added in 4 portions during 5 minutes, stirred for 1.5 hours at −78° C. and left to worm up to room temperature overnight. At stirring 0.1 M sodium hydroxide solution (2.5 ml) was slowly added to reach pH 12 then extracted with 15×5 ml diethyl ether. The combined organic solutions were dried over magnesium sulfate and evaporated at 35° C. on rotavapor. The residue (0.0336 g) was chromatographed first on 3 g silica gel with diethyl ether containing at the beginning 10 percent of diethylamine which was raised to 20 percent giving the a less polar fraction which was further purified by preparative HPLC furnishing the pure cis-compound; while the more polar fractions were further purified on 2 g silica gel with tert-butyl methyl ether containing 30 percent of diethylamine furnishing the pure trans-compound. The cis and trans configuration of the substituents on the 2 and 4 position of the azetidine ring of the two compounds were determined by nuclear Overhauser experiments.

Cis-3-(1,4-Dimethylazetidin-2-yl)pyridine $^1$H-NMR: 8.54 (1H, dd, J=4.8, 1.5 Hz), 8.50 (1H, d, J=2.4 Hz), 7.55 (1H, dt, J=7.8, 1.8 Hz), 7.31 (1H, dd, J=7.8, 4.8 Hz), 4.01-4.12 (1H, m), 3.71 (1H, dd, J=10.5, 3.9 Hz), 2.26 (3H, s), 1.59-1.82 (2H, m), 1.18 (3H, d, J=6.0 Hz).

Trans-3-(1,4-Dimethylazetidin-2-yl)pyridine $^1$H-NMR: 8.52-8.56 (2H, m), 7.68 (1H, dt, J=7.5, 1.8 Hz), 7.31 (1H, ddd, J=7.8, 4.8, 0.6 Hz), 3.96 (1H, dd, J=6.6, 4.5 Hz), 3.84-3.94 (1H, m), 2.36 (3H, s), 1.74-1.91 (2H, m), 1.18 (3H, d, J=6.0 Hz).

Example 3

In this example it is demonstrated that the effects of 5'-alkylation of the pyrrolidine ring of nicotine also are obtained when the pyrrolidine ring is only indirectly attached to the 3-pyridyl ring of nicotine. That is, an additional group or segment connecting the pyrrolidinyl ring to the pyridine ring can be present and the effect of alkylation at a carbon (in this case 5' position) is still observed. Several types of linker have already been published (examples: -methylene group-, -methyleneoxy-) for alpha4beta2 ligands. In this example a diastereomeric 5'-methyl-(S)-nicotine analog containing a methyleneoxy linker has been synthesized to test whether the 5' trans-methyl pyrrolidinyl substituent retains an advantage over the 5-cis-methyl substituent for selective stimulation of alpha7 nAChRs.

Synthesis of 3-((2S,5R)- and 3-((2S,5S)-1,5-Dimethylpyrrolidin-2-yl)methoxy)pyridines (S)-Methyl 1-methyl-5-oxopyrrolidine-2-carboxylate To a stirred suspension of 2.0 g (50 mmole) 60% sodium hydride dispersion in mineral oil in 50 ml of degassed dry dimethylformamide at room temperature under argon atmosphere 2.58 g (20 mmole) L-pyroglutamic acid was added during 15 minutes and stirred at room temperature for 8 hours. While ice cooling and stirring, 3.11 ml (7.10 g, 50 mmole) iodomethane was added while stirring and allowed to warm to room temperature overnight. After adding 0.4 ml of acetic acid, the mixture (pH 5) was evaporated at 35° C. in good vacuum to remove the dimethylformamide, then 25 ml of dichloromethane was added, the solution stirred for 30 minutes, cooled with ice bath and filtered. The mother liquor was evaporated at 35° C. in good vacuum; the residue was washed with 3×10 ml of hexane then suspended in 25 ml of chloroform, stirred for 15 minutes and filtered. The chloroform solution was washed with 5×10 ml of water, dried over magnesium sulfate and evaporated in good vacuum. The residue was washed with 6×5 ml of dry hexane; removal of traces of hexane at 35° C. in good vacuum furnished the pure product as a pale brown liquid.

$^1$H-NMR: 4.13 (1H, dd, J=5.7, 3.3 Hz), 3.78 (3H, s), 2.85 (3H, s), 2.26-2.37 (3H, m), 2.01-2.15 (1H, m).

$^{13}$C-NMR: 175.16, 172.21, 61.69, 52.44, 29.22, 28.90, 22.67.

(S)-5-(Hydroxymethyl)-1-methylpyrrolidin-2-one

A stirred solution of 0.68 g (4.33 mmole) (S)-Methyl 1-methyl-5-oxopyrrolidine-2-carboxylate in 15 ml dry tetrahydrofuran was cooled to −78° C. and under argon atmosphere, 2.2 ml (2.2 mmole) of 1M lithium aluminum hydride solution in tetrahydrofuran was added drop by drop during 20 minutes, stirred at −78° C. for 1 hour and removing the cooling bath left to warm up to 0° C. at stirring. While ice cooling, 0.22 ml 10% of sodium hydroxide aqueous solution was added, stirred for 10 minutes, then 0.22 ml of water was added and the reaction mixture stirred for 1.5 hours allowing it to warm to room temperature. The precipitate was filtered and washed with 5×2 ml of ethyl acetate. The combined filtrates were dried over magnesium sulfate and evaporated at 35° C. in good vacuum, giving 0.52 g (93%) product which was pure enough for the next step.

$^1$H-NMR: 3.86 (1H, J=11.4, 3.3 Hz), 3.62-3.51 (2H, m), 2.88 (3H, s), 2.54-2.41 (1H, m), 2.40-2.24 (1H, m), 2.19-2.05 (1H, m), 2.03-1.90 (1H, m).

$^{13}$C-NMR: 175.94, 62.69, 61.40, 30.31, 28.10, 20.82.

(S)-1-Methyl-5-((pyridin-3-yloxy)methyl)pyrrolidin-2-one

To a stirred solution of 1.57 g (6.0 mmole) triphenylphosphine in 30 ml dry tetrahydrofuran under argon atmosphere at −15° C. 0.95 ml (1.05 g, 6.0 mmole) diethyl azodicarboxylate was added, drop by drop for 5 minutes, then 0.517 g (4.0 mmole) (S)-5-(hydroxymethyl)-1-methylpyrrolidin-2-one in 5 ml dry tetrahydrofuran and 0.40 g (4.2 mmole) 3-hydroxypyridine were added and stirred for 10 minutes, then kept overnight in a refrigerator at −20° C. The solution was evaporated at 35° C. in good vacuum; the residue was dissolved in 15 ml of dichloromethane and washed with 1×7 and 2×2 ml of 1M hydrochloric acid. To the combined acidic solutions 20 ml saturated aqueous sodium bicarbonate solution was carefully added and then further 1 g of solid sodium bicarbonate was added, and this was extracted with 5×10 ml dichloromethane. The combined organic solutions were dried over magnesium sulfate, evaporated on a rotavapor at 35° C. and the residue was purified by column chromatography on 30 g silica gel, and developing with benzene containing 30% of diethylamine; this furnished 0.252 g (31%) of pure product.

$^1$H-NMR: 8.32 (1H, dd, J=2.7, 0.6 Hz), 8.27 (1H, dd, J=4.5, 1.5 Hz), 7.26-7.17 (2H, m), 4.14 (1H, dd, J=9.9, 3.9 Hz), 4.04 (1H, dd, J=9.6, 4.5 Hz), 3.92 (1H, sextet, J=4.2 Hz), 2.92 (3H, s), 2.62-2.49 (1H, m), 2.47-2.34 (1H, m), 2.34-2.20 (1H, m), 2.03-1.91 (1H, m).

$^{13}$C-NMR: 175.26, 154.51, 142.89, 137.57, 123.93, 121.37, 68.99, 59.01, 29.91, 28.43, 21.45.

3-(((2S,5S)- and 3-(((2S,5R)-1,5-Dimethylpyrrolidin-2-yl)methoxy)pyridine

To a stirred solution of 0.121 g (0.587 mmole) (S)-1-Methyl-5-((pyridin-3-yloxy)methyl)pyrrolidin-2-one in 10 ml of dry tetrahydrofuran under argon atmosphere at ice cooling, 1.10 ml (1.76 mmole) of 1.6M methyllithium solution in diethyl ether was added drop by drop for 5 minutes and stirred for 5 minutes under ice cooling, and then at room temperature for 1 hour. To this reaction mixture at room temperature and while stirring, 2.95 ml (2.95 mmole) 1M lithium aluminum hydride solution in tetrahydrofuran was added in 3 minutes and stirred for 1 hour. First 0.29 ml of 10% sodium hydroxide aqueous solution was added drop by drop and after 10 minutes stirring 0.29 ml water was added and stirred for 2 hours. The precipitate was filtered and it was washed with 5×5 ml of ethyl acetate, the combined organic solutions were evaporated at 35° C. in good vacuum. The residue (0.102 g) was separated with column chromatography on 10 g silica gel with cyclohexane-diethylamine (80-20, v/v) giving the more polar 3-(((2S,5R)-1,5-dimethylpyrrolidin-2-yl)methoxy)pyridine in pure form (5.42 mg, 4.5%). From the less polar fractions with column chromatography on 2 g silica gel we got the pure 3-(((2S,5S)-1,5-Dimethylpyrrolidin-2-yl)methoxy)pyridine (1.12 mg, 9%) isomer. The cis and trans configurations of the substituents at the 1 and 5 positions of the pyrrolidine ring were determined by nuclear Overhauser experiments.

3-(((2S,5S)-1,5-Dimethylpyrrolidin-2-yl)methoxy)pyridine $^1$H-NMR: 8.33-8.31 (1H, m), 8.22-8.19 (1H, m), 7.21-7.19 (2H, m), 4.04 (1H, dd, J=9.0, 5.4 Hz), 3.89 (1H, dd, J=9.0, 6.3 Hz), 2.83-2.72 (1H, m), 2.41 (3H, s), 2.44-2.34 (1H, m), 2.06-1.83 (1H, m), 1.70-1.60 (1H, m), 1.52-1.37 (1H, m), 1.13 (1H, d, J=6.3 Hz).

3-(((2S,5R)-1,5-Dimethylpyrrolidin-2-yl)methoxy)pyridine $^1$H-NMR: 8.34-8.31 (1H, m), 8.23-8.19 (1H, m), 7.22-7.18 (2H, m), 4.01 (1H, dd, J=9.0, 4.5 Hz), 3.91 (1H, dd, J=9.3, 5.4 Hz), 3.25-3.08 (2H, m), 2.46 (3H, s), 2.22-1.97 (2H, m), 1.77-1.66 (1H, m), 1.55-1.42 (1H, m), 1.02 (3H, d, J=6.3 Hz).

Methods of Functional Analysis of Nicotinoid Stimulation of Different nAChRs Xenopus Oocyte Expression System Mature female Xenopus laevis were anesthetized by immersion in a 1.5 g/L solution of aminobenzoic acid ethyl ester (MP Biomedicals, LLC, Solon, Ohio) for 30 min. The excised ovary bag was placed into calcium-free Barth's saline (88 mM NaCl, 1 mM KCl, 2.38 mM NaHCO3, 0.82 mM MgSO4, 15 mM HEPES, 0.012 mg/ml tetracycline hydrochloride, pH 7.3+−0.1), opened with forceps and washed three times with Barth's saline. Then 60 ml collagenase solution (76 mg Sigma type XX collagenase dissolved in $Ca^{2+}$-free Barth saline) was added and the oocyte containing mass was shaken for 2 hours at 5° C. After washing three times with $Ca^{2+}$-free Barth's and then three times with Barth's solution containing calcium, the oocytes were evaluated under a stereo microscope. Healthy stage 5 oocytes were transferred into new dishes and incubated in 17° C. for overnight. Oocytes were injected with either 50 nl of alpha7 mRNA solution (20 ng) or 50 nl of a mixture of alpha4 and beta2 (1:1, 10 ng) mRNA, using a Drummond Nanoject II Auto-Injector. The cells were cultured in Barth's saline at 17° C. for 5-16 days, with daily changes in the saline. Individual oocytes were placed in a 0.5 ml oocyte perfusion chamber (Bioscience Tools) and perfused at room temperature with Barths saline (115 mM NaCl, 2.5 mM KCl, 10 mM HEPES, 1.8 mM $CaCl_2$, pH 7.3) containing 1 μM atropine to block potential muscarinic responses. The two-microelectrode voltage-clamp technique was used to measure current responses at a constant holding potential (−60 mV for a7 and −50 mV for a4b2n AChRs). The voltage-measuring microelectrode (filled with 3M KCl solution) electric resistance was 0.5-3 MS: the current-passing electrode (containing 250 mM CsCl, 250 mM CsF and 100 mM EGTA). Membrane currents were recorded with an AxoClamp-2 (Axon Instruments, Union City, Calif.), filtered at 10 kHz and sampled at 5 kHz. All compound applications were separated by a wash period of 5 min. Salines containing test or ACh (control) concentrations were rapidly applied using a ValveLink8.2® controller (AutoMate Scientific, San Francisco, Calif.). Flow rates were 2 ml/min for a7 receptor experiments and 4 ml/min for a4b2 receptors. Initially each oocyte received three control applications of ACh (1 mM for a7 and 100 μM ACh for a4b2 receptors). ACh control applications alternated with test compound applications. The peak current response to a given compound concentration was normalized with respect to the mean current response to ACh applications before and after the test concentration. Clampfit 8.1 (Axon Instruments) and Prism 3.0 (La Jolla, Calif., USA) softwares were used for data acquisition and analysis, respectively. The concentration-response curve for each compound and receptor subtype was fitted with the Hill equation, where apparent cooperativity n=Hill slope. The number of cells (n) tested at each concentration was generally >4 and is given in each table or figure. Data for peak current responses and for potency estimates ($EC_{50}$s) are presented as means±S.E.M.

Radioligand Binding Experiments with Rat Brain and Human nAChRs

Protocols for radioligand binding experiments with rat brain membranes have been previously described (Kem et al., 2004). Whole male Sprague-Dawley rat brains (Pel-Freeze Biologicals, Rogers, Ariz.) were homogenized with a 30 ml Wheaton (location) glass homogenizing tube and pestle in binding saline (120 mM NaCl, 5 mM KCl, 2 mM $CaCl_2$, 1 mM $MgCl_2$, 50 mM Tris-TrisHCl buffer, pH 7.4). After the homogenate was centrifuged at 11,000 rpm (convert to x G) for a 10 min, the resulting pellet was resuspended in fresh binding saline and homogenized and centrifuged again. A protein assay (BCA, Pierce, Rockford, Ill.) was then performed to obtain the protein concentration of the rat brain membranes contained in the pellet, which was stored at −85° C. before use. The radioligands used in the displacement binding assays were obtained from Perkin Elmer Life and Analytical Sciences (Boston, Mass.). $^3$H-Cytisine (34 Ci/mmol) experiments were performed according to Flores et al. (1992) with a few minor alterations, specifically that the incubation time was increased to four hours at 4° C. to assure binding equilibrium. The $^{125}$I-α-bungarotoxin (α-Btx) (136 Ci/mmol) experiments involved 37° C. incubation for three hours to assure equilibration. Both radioligands were used at a final concentration of 1 nM. Membranes at the above mentioned concentrations were suspended in binding saline containing 2 mg/ml of bovine serum albumin (Sigma, St. Louis, Mo.) to reduce non-specific binding. The tsa cell membranes, radioligand and compound of interest were incubated together in 13×100 mm disposable glass culture tubes in a final volume of 0.5 ml. For each radioligand nonspecific binding was measured in the presence of a final concentration of 1 mM (S)-nicotine hydrogen tartrate salt (Sigma, St. Louis, Mo.). After incubation, radioligand bound to membranes in 48 tubes was rapidly collected by vacuum filtration using a Brandel cell harvester (Gaithersburg, Md.) and Whatman GF/C glass fiber filters that were pre-soaked in 0.5% polyethylenimine for 45 minutes to reduce nonspecific binding. The radiolabeled membranes were rapidly washed three times with 3 ml ice-cold binding saline to separate bound from free radioligand. Filters containing $^3$H-cytisine bound membranes were collected in 20 ml scintillation tubes and suspended in 8 mls of 30% Scintisafe scintillation fluid (Fisher), then counted in a Beckman LS-6500 liquid scintillation counter (Fullerton, Calif.). Filters containing $^{125}$I-α-Btx bound membranes were placed in 4 ml scintillation vials and counted in a Beckman 5500B gamma counter (Fullerton, Calif.).

Displacement assay binding data were analyzed using GraphPad Prism software (San Diego, Calif.). The mean counts per minute values for each concentration of a given compound concentration were obtained from 3 (tsa cells) or 4 (brain membrane experiments) replicates. The data were fitted to a sigmoidal concentration response curve with variable slope, from which the Hill slope and $IC_{50}$ values were determined. The $IC_{50}$ value along with the pre-determined $K_d$ value for the radioligand and nAChR-containing membrane of interest were then used in the Cheng Prusoff equation ($K_i = IC_{50}/(1+(Ligand)/K_d)$) to calculate the $K_i$ value. Differences between means estimates were compared using an unpaired, two-tailed T-test in GraphPad Prism.

FIG. 4.1 illustrates the synthesis and separation of 3-(((2S,5R)-1,5-Dimethylpyrrolidine-2-yl)methoxy)-pyridine (Trans) and 3-(((2S,5S)-1,5-Dimethylpyrrolidine-2-yl)methoxy)pyridine (Cis).

FIG. 4.2 illustrates the starting reagent for synthesis of the methoxypyridine analogs of nicotine.

FIG. 4.3 illustrates the N-methylpyrrolidinone precursor.

FIG. 4.4 illustrate the intermediate in the synthesis of 3-(((2S,5R)-1,5-Dimethylpyrrolidine-2-yl)methoxy)-pyridine (Trans) and 3-(((2S,5S)-1,5-Dimethylpyrrolidine-2-yl)methoxy)pyridine (Cis).

FIG. 4.5 illustrates the synthesis and separation of 3-(((2S,5S)-1,5-Dimethylpyrrolidine-2-yl)methoxy)-pyridine (Trans enantiomer with low activity on alpha4beta2 receptors but high potency on alpha7 receptors).

FIG. 4.6 illustrates the synthesis and separation of 3-(((2S,5S)-1,5-Dimethylpyrrolidine-2-yl)methoxy)-pyridine (Cis enantiomer with low activity on alpha4beta2 and alpha7 receptors).

FIG. 4.7 illustrates both enantiomers, 3-(((2S,5R)-1,5-Dimethylpyrrolidine-2-byl)methoxy)pyridine (■) and 3-(((2S,5S)-1,5-Dimethylpyrrolidine-2-yl)methoxy)pyridine (♦) display essentially no agonistic activity on α4β2 receptors (n≥3) expressed in the *Xenopus* oocytes.

It should be noted for the synthesis steps described, the components (e.g., methyl iodide can be alkyl halogenide) in the reactions can be changed consistent with teachings described herein.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

While only a few embodiments of the present disclosure have been shown and described herein, it will become apparent to those skilled in the art that various modifications and changes can be made in the present disclosure without departing from the spirit and scope of the present disclosure. All such modification and changes coming within the scope of the appended claims are intended to be carried out thereby.

We claim at least the following:

1. A compound having the formula:

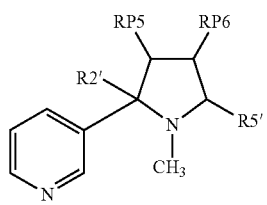

wherein:
R2' is selected from the group consisting of: methyl, ethyl, propyl, hydroxymethyl, an amide, and methylamine; and
R5', RP5, and RP6 are independently H, or a substituted or unsubstituted group selected from: an aliphatic group, an alkoxy group, a cycloalkyl group, an aryl group, a heteroaryl group, and a heterocyclic group;
and wherein when R2' is methyl, then at least one of R5', RP5, and RP6 is not H.

2. The compound of claim 1, wherein R2' is a methyl group, ethyl group, or a propyl group.

3. The compound of claim 1, wherein R2' is —CH$_2$NH$_2$, —CH$_2$OH, or —CONH$_2$.

4. The compound of claim 1, wherein R2' is a methyl group, ethyl group, or a propyl group.

5. The compound of claim 1, wherein R5' is at the trans position relative to R2'.

6. The compound of claim 1, wherein R5' is at the cis position relative to R2'.

7. A compound having the formula:

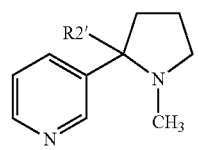

wherein R2' is selected from the group consisting of: ethyl, propyl, hydroxymethyl, an amide, and methylamine.

8. The compound of claim 7, wherein R2' is a ethyl group, or a propyl group.

9. The compound of claim 7, wherein R2' is —CH$_2$NH$_2$, —CH$_2$OH, or —CONH$_2$.

10. A compound having the formula:

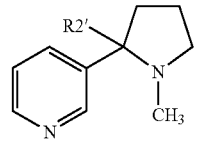

wherein R2' is selected from the group consisting of: ethyl, propyl, hydroxymethyl, an amide, and methylamine, wherein one or more of the hydrogens of each of the rings is substituted with an R group, wherein each R group is independently a substituted or unsubstituted group selected from: an aliphatic group, an alkoxy group, a cycloalkyl group, an aryl group, a heteroaryl group, and a heterocyclic group.

* * * * *